(12) United States Patent
Huang et al.

(10) Patent No.: US 12,396,814 B2
(45) Date of Patent: Aug. 26, 2025

(54) CONTROL METHOD FOR SURGICAL ROBOTIC ARM, COMPUTER DEVICE, AND SURGICAL ROBOTIC ARM

(71) Applicant: NOAHTRON INTELLIGENCE MEDTECH (HANGZHOU) CO., LTD., Zhejiang (CN)

(72) Inventors: Shandeng Huang, Zhejiang (CN); Long Bai, Zhejiang (CN); Xiaohong Chen, Zhejiang (CN); Jianfei Liu, Zhejiang (CN)

(73) Assignee: NOAHTRON INTELLIGENCE MEDTECH (HANGZHOU) CO., LTD., Zhejiang (CN)

( * ) Notice: Subject to any disclaimer, the term of this patent is extended or adjusted under 35 U.S.C. 154(b) by 342 days.

(21) Appl. No.: 17/794,949

(22) PCT Filed: Jul. 15, 2020

(86) PCT No.: PCT/CN2020/101996
§ 371 (c)(1),
(2) Date: Jul. 22, 2022

(87) PCT Pub. No.: WO2021/147265
PCT Pub. Date: Jul. 29, 2021

(65) Prior Publication Data
US 2023/0270514 A1    Aug. 31, 2023

(30) Foreign Application Priority Data

Jan. 23, 2020 (CN) .......................... 202010076419.0

(51) Int. Cl.
*A61B 34/35*    (2016.01)
*A61B 34/30*    (2016.01)
(Continued)

(52) U.S. Cl.
CPC ............. *A61B 34/35* (2016.02); *B25J 9/1689* (2013.01); *B25J 18/00* (2013.01); *A61B 2034/304* (2016.02); *A61B 2090/061* (2016.02)

(58) Field of Classification Search
CPC .............. A61B 34/35; A61B 2034/304; A61B 2090/061; A61B 34/32; A61B 34/71;
(Continued)

(56) References Cited

U.S. PATENT DOCUMENTS

| | | |
|---|---|---|
| 4,819,496 A | 4/1989 | Shelef |
| 5,053,687 A | 10/1991 | Merlet |

(Continued)

FOREIGN PATENT DOCUMENTS

| | | |
|---|---|---|
| CA | 2770507 A1 | 2/2011 |
| CA | 3035284 A1 | 3/2018 |

(Continued)

OTHER PUBLICATIONS

Zhai Qing-Zhong et al., The research of six axis parallel machine tools based on the Stewart platform, Mechanical and Electrical Engineering Department, Shihezi University, Shihezi 832000, China.

(Continued)

*Primary Examiner* — Sohana Tanju Khayer
(74) *Attorney, Agent, or Firm* — Bridgeway IP Law Group, PLLC; Sang Ho Lee; Hyun Woo Shin

(57) ABSTRACT

A control method for a surgical robotic arm, a computer device and a surgical robotic arm are provided. The control method includes calculating a telecentric fixed point on an executing rod according to a target point and controlling a preoperative positioning assembly to advance a first movable platform of a telecentric manipulating assembly along a first coordinate axis of a movable coordinate system; calculating a first origin coordinate of an origin of the first movable platform in a stationary coordinate system accord- (Continued)

ing to the coordinate of the telecentric fixed point and the trajectory coordinate of an end point; calculating the length of a first telescopic element of the telecentric manipulating assembly according to the coordinates of a hinge point of the telecentric manipulating assembly in the stationary coordinate system; and controlling the first movable platform to move to a designated pose.

29 Claims, 9 Drawing Sheets

(51) Int. Cl.
    *A61B 90/00*     (2016.01)
    *B25J 9/16*     (2006.01)
    *B25J 18/00*     (2006.01)

(58) Field of Classification Search
    CPC ......... A61B 34/30; B25J 9/1689; B25J 18/00; B25J 9/0075; B25J 9/0057; Y02P 90/02
    See application file for complete search history.

(56) References Cited

U.S. PATENT DOCUMENTS

| | | | |
|---|---|---|---|
| 5,279,309 | A | 1/1994 | Taylor et al. |
| 5,651,574 | A | 7/1997 | Tanikawa et al. |
| 5,987,726 | A | 11/1999 | Akeel |
| 6,477,912 | B2 | 11/2002 | Song et al. |
| 12,089,910 | B2* | 9/2024 | Zhang .................... A61B 34/73 |
| 2003/0106230 | A1 | 6/2003 | Hennessey |
| 2010/0122602 | A1 | 5/2010 | Marcroft et al. |
| 2011/0282358 | A1* | 11/2011 | Gomez ................ G03B 35/00 606/130 |
| 2014/0194699 | A1 | 7/2014 | Roh et al. |
| 2015/0005785 | A1 | 1/2015 | Olson |
| 2016/0249990 | A1 | 9/2016 | Glozman et al. |
| 2016/0361128 | A1* | 12/2016 | Seeber .................... A61B 34/30 |
| 2017/0112579 | A1 | 4/2017 | Yen et al. |
| 2018/0000548 | A1 | 1/2018 | Olds et al. |
| 2018/0333207 | A1* | 11/2018 | Moctezuma De la Barrera .......... A61B 34/30 |
| 2019/0060014 | A1 | 2/2019 | Hazelton et al. |
| 2019/0125461 | A1 | 5/2019 | Zheng et al. |
| 2019/0380795 | A1 | 12/2019 | Tsao et al. |
| 2020/0009001 | A1 | 1/2020 | Xue et al. |
| 2021/0192759 | A1* | 6/2021 | Lang ..................... A61B 90/98 |
| 2022/0280193 | A1* | 9/2022 | Tal ....................... A61B 17/42 |
| 2022/0409282 | A1* | 12/2022 | Shochat ................ A61B 34/32 |
| 2023/0255701 | A1* | 8/2023 | Post ....................... A61B 34/30 606/82 |

FOREIGN PATENT DOCUMENTS

| | | |
|---|---|---|
| CN | 101400476 A | 4/2009 |
| CN | 101919739 A | 12/2010 |
| CN | 102179807 A | 9/2011 |
| CN | 102429726 A | 5/2012 |
| CN | 102892375 A | 1/2013 |
| CN | 104546147 A | 4/2015 |
| CN | 104739487 A | 7/2015 |
| CN | 105965557 A | 9/2016 |
| CN | 106725855 A | 5/2017 |
| CN | 107037823 A | 8/2017 |
| CN | 107336231 A | 11/2017 |
| CN | 107775627 A | 3/2018 |
| CN | 108015750 A | 5/2018 |
| CN | 108697481 A | 10/2018 |
| CN | 109199591 A | 1/2019 |
| CN | 109316241 A | 2/2019 |
| CN | 109998687 A | 7/2019 |
| CN | 110693611 A | 1/2020 |
| CN | 111214291 A | 6/2020 |
| CN | 111227943 A | 6/2020 |
| ES | 2390436 A1 | 11/2012 |
| IN | 208598522 U | 3/2019 |
| JP | 2017-104450 A | 6/2017 |
| WO | 2011/143024 A1 | 11/2011 |
| WO | 2013/067535 A1 | 5/2013 |
| WO | 2015/168799 A1 | 11/2015 |

OTHER PUBLICATIONS

Wen Jin-Hai, Posture equation and dynamics reverse solution of Stewart typed parallel machine tools based on D-H transformation matrix, Published 2009 Materials Science Journal of Machine Design.

Wen Gang, Research on control algotithn of 6-DOF parallel Robot, May 2017, Chian Academic Journal Electronic Publishing House, http://www.cnki.net.

Tsui, Irena et al., "Robotic Surgery in Ophthalmology", Robot Surgery, Jan. 2010, Intech, Croatia.

Zhang, Zhenchuan et al., "Design and Kinematic Analysis of A Parallel Robot with Remote Center of Motion for Minimally Invasive Surgery", Proceedings of 2015 IEEE, International Conference on Mechatronics and Automation (ICMA), Aug. 2-5, 2015, Beijing, China.

Gallardo-Alvarado, Jaime et al., "Kinematics and dynamics of 2(3-RPS) manipulators by means of screw theory and the principle of virtual work", Mechanism and Machine Theory, vol. 43, No. 10 (2008), pp. 1281-1294, Oct. 1, 2008.

Kucuk, Serdar et al., "Inverse Kinematics Solution of a New Hybrid Robot Manipulator Proposed for Medical Purposes," 2016 Medical Technologies National Congress (TIPTEKNO), Oct. 29, 2016, Antalya, Turkey.

* cited by examiner

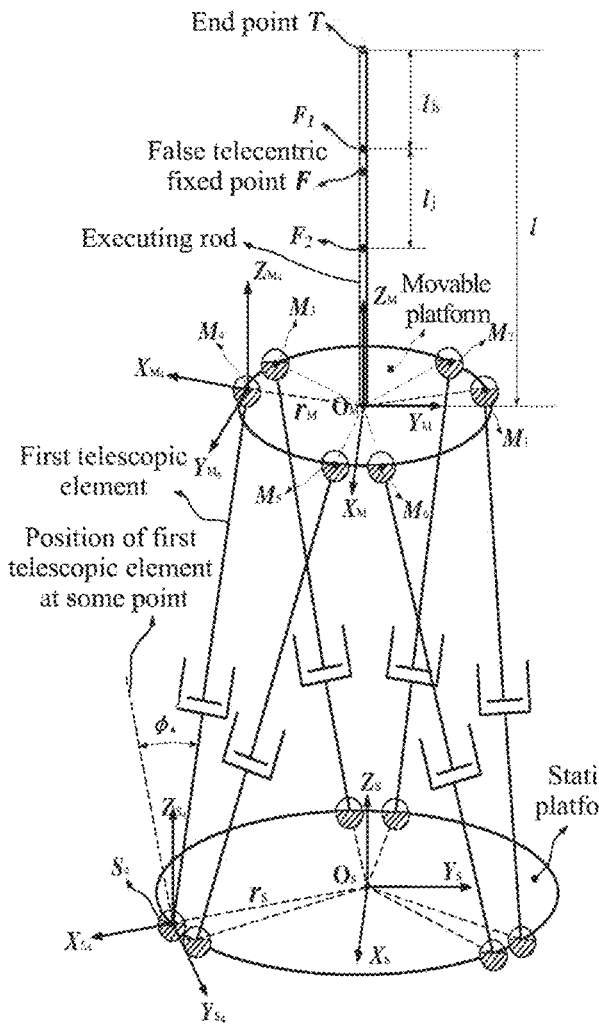 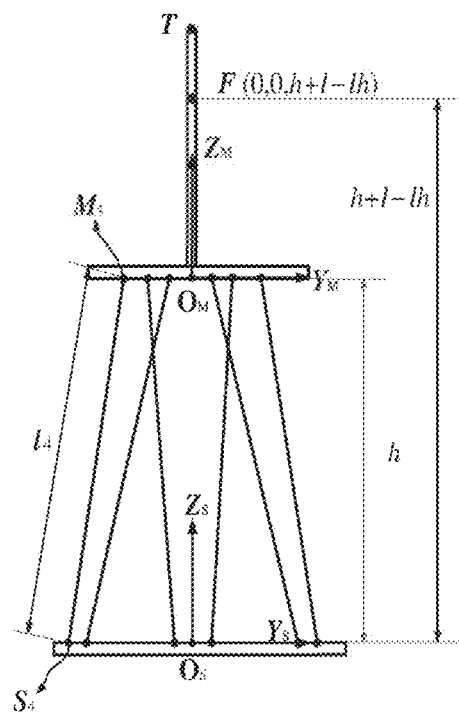
FIG. 3A
FIG. 3B
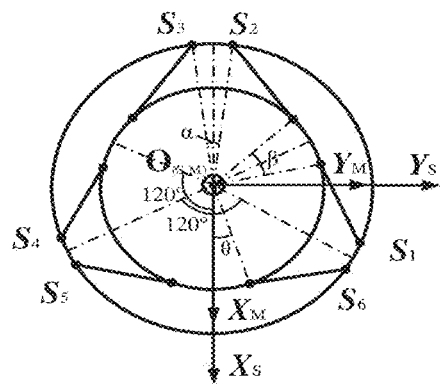
FIG. 3C

CONTROL METHOD FOR SURGICAL ROBOTIC ARM, COMPUTER DEVICE, AND SURGICAL ROBOTIC ARM

RELATED APPLICATIONS

The present application claims the right of priority of Chinese patent application filed on Jan. 23, 2020 with the application No. 202010076419.0 and the title of invention "CONTROL METHOD FOR SURGICAL ROBOTIC ARM, COMPUTER DEVICE AND SURGICAL ROBOTIC ARM", of which all the contents are incorporated into the present application by reference.

TECHNICAL FIELD

The present disclosure relates to the technical field of medical equipment, particularly to a control method for a surgical robotic arm, a computer device and a surgical robotic arm.

BACKGROUND ART

With the development of science and technology, surgical robots have greatly increased the flexibility of surgical operations. Doctors can perform more sophisticated operations. In this case, incorporating ergonomics design can reduce the fatigue of doctors. In related technologies, a doctor sends a control command through remote operation, and then the control system makes the surgical equipment at the end of several (generally 4-6) surgical robotic arms of the surgical robot, such as Da Vinci surgical robot, into a patient's body according to the control command, and deflects different angles to pass through the heart or lungs to the focus for surgery; therefore, in related technologies, surgical robots usually have large and complex structures. In order to complete the corresponding surgical operations, especially when the movement range of the end of equipment is large, the robotic arms of the surgical robot are prone to interference, which is not conducive to the implementation of minimally invasive surgeries.

There is no effective solution to the problem of large structural size of surgical robotic arms and interference between surgical robotic arms in related technologies.

SUMMARY

A control method for a surgical robotic arm, a computer device and a surgical robotic arm are provided according to various embodiments of the present disclosure.

According to one aspect of various embodiments of the present disclosure, a control method for a surgical robotic arm is provided, the surgical robotic arm includes a preoperative positioning assembly and an active arm, the active arm includes an executing rod and a telecentric manipulating assembly, the executing rod is connected to the telecentric manipulating assembly and the telecentric manipulating assembly is connected to the preoperative positioning assembly. The method includes:

calculating a telecentric fixed point on the executing rod according to a target point, and controlling the preoperative positioning assembly to advance a first movable platform of the telecentric manipulating assembly along a first coordinate axis of a movable coordinate system, and the advanced distance is equal to a distance from the obtained telecentric fixed point to an end point on the executing assembly;

calculating a first origin coordinate of an origin of the first movable platform in a stationary coordinate system according to the coordinate of the telecentric fixed point and the trajectory coordinate of the end point;

calculating the length of a first telescopic element of the telecentric manipulating assembly according to the coordinates of a hinge point of the telecentric manipulating assembly in the stationary coordinate system; and controlling the first movable platform to move to a designated pose, and the designated pose is determined according to the first origin coordinate and the length of the first telescopic element.

According to another aspect of various embodiments of the present disclosure, a surgical robotic arm is provided and includes a preoperative positioning assembly, a telecentric manipulating assembly, an executing assembly and a control system. The preoperative positioning assembly is connected to the telecentric manipulating assembly. The telecentric manipulating assembly is connected to the executing assembly;

the control system calculates a telecentric fixed point on the executing rod of the executing assembly according to a target point, and controls the preoperative positioning assembly to advance a first movable platform of the telecentric manipulating assembly along a first coordinate axis of a movable coordinate system, and the advanced distance is equal to a distance from the obtained telecentric fixed point to an end point on the executing assembly;

the control system calculates a first origin coordinate of an origin of the first movable platform in a stationary coordinate system according to the coordinate of the telecentric fixed point and the trajectory coordinate of the end point;

the control system calculates the length of the first telescopic element of the telecentric manipulating assembly according to the coordinates of a hinge point of the telecentric manipulating assembly in the stationary coordinate system; and the control system controls the first movable platform to move to a designated pose, and the designated pose is determined according to the first origin coordinate and the length of the first telescopic element.

According to another aspect of various embodiments of the present disclosure, a computer device is provided and includes a memory, a processor and a computer program which is stored on the memory and may run on the processor, and the processor implements steps of any method according to various embodiments of the present disclosure while executing the computer program.

According to another aspect of various embodiments of the present disclosure, a computer readable storage medium is provided, on which a computer program is stored, and the computer program implements steps of any method according to various embodiments of the present disclosure while being executed by a processor.

BRIEF DESCRIPTION OF THE DRAWINGS

In order to better describe and explain those embodiments and/or examples disclosed herein, reference may be made to one or more figures. Additional details or examples for describing the accompanying drawings should not be considered as limiting the scope of any of the disclosed, currently described embodiments and/or examples as well as these currently understood best modes.

FIG. 3A is an axial view of a telecentric manipulating assembly according to embodiments of the present disclosure;

FIG. 3B is a front view of a telecentric manipulating assembly according to embodiments of the present disclosure;

FIG. 3C is a top view of a telecentric manipulating assembly according to embodiments of the present disclosure;

DETAILED DESCRIPTION OF EXEMPLARY EMBODIMENTS

In order to make the purpose, technical solution and advantages of the present disclosure clearer, the present disclosure is further described in detail below in combination with the accompanying drawings and embodiments. It should be understood that detailed embodiments described herein are only used for explaining the present disclosure but not used for limiting the present disclosure.

Figure 1:
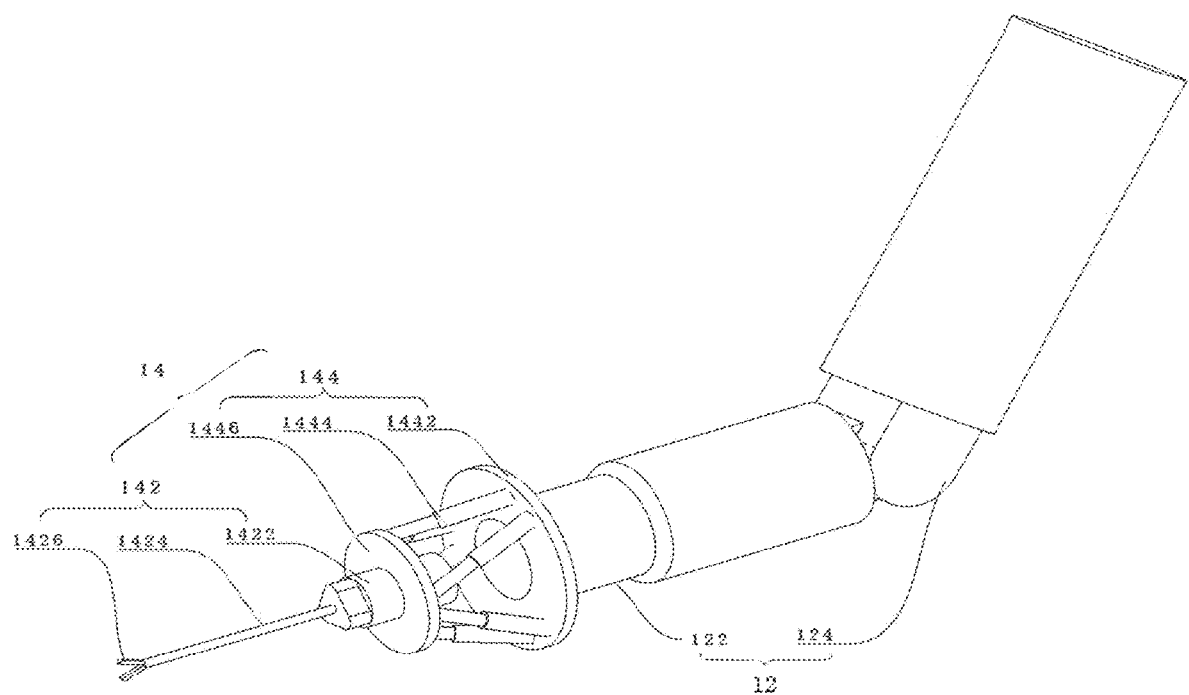
FIG. 1 is a diagram of a model of a surgical robotic arm according to embodiments of the present disclosure.

In the present embodiment, a model of a surgical robotic arm is provided. FIG. 1 is a diagram of a model of a surgical robotic arm according to embodiments of the present disclosure, as illustrated in FIG. 1. The surgical robotic arm includes a preoperative positioning assembly 12 and an active arm 14. The preoperative positioning assembly 12 includes a telescopic mechanism 122 and a rotational mechanism 124; the telescopic mechanism 122 performs a telescopic motion to control a telescopic position, which is mainly used for preoperative positioning; and the rotational mechanism 124 is used for preoperative positioning and adjusting a position of a mechanism.

The active arm 14 includes an executing assembly 142 and a telecentric manipulating assembly 144; the executing assembly 142 includes a driving member 1422, an executing rod 1424 and a surgical instrument 1426, the executing rod 1424 and the surgical instrument 1426 are connected via a rotational joint, the edges of the executing rod 1424 and the rotational joint are smooth transition without edges and corners, so as to avoid injury to human body or organs; the executing rod 1424 is internally provided with a steel wire rope to control the action of the surgical instrument 1426, and the driving member 1422 is used for driving the steel wire rope to move, thereby driving and controlling the rotation of the three degrees of freedom of the executing rod 1424 and controlling the action of clamping tissues of the surgical instrument 1426.

The telecentric manipulating assembly 144 is a spatial parallel mechanism composed of an end effector with multiple directions of movement connected with another fixed end of a mechanical system through a hinge and a telescopic mechanism, and the telecentric manipulating assembly 144 may be a Stewart parallel platform which includes a static platform 1442, six first telescopic elements 1444 and a first movable platform 1446; the static platform 1442 is connected with the six first telescopic elements 1444 by U pairs of hinges, and the static platform 1442 may rotate in the x axis and y axis directions, but limits the degree of freedom in the z axis direction; the first telescopic element 1444 may be a driving rod, which is composed of an electrode and a lead screw, an electric cylinder may be freely telescopic by driving the lead screw through the electrode, so as to change the motion state of the first movable platform 1446, and the six first telescopic elements 1444 are arranged according to a certain rule, so that the deflection angle of the Stewart parallel platform is small, and the deflection angle range between the first telescopic element 1444 and the z axis is within ±20°; the diameter of the first movable platform 1446 is smaller than that of the static platform 1442, the motion state of the first movable platform 1446 is controlled by the length change of the first telescopic element 1446, and the first movable platform 1446 and the first telescopic element 1444 may implement rotation in three directions of x axis, y axis and z axis by means of a ball hinge; and in the movable coordinate system and the stationary coordinate system, a first coordinate axis is z axis, a second coordinate axis is x axis, and a third coordinate axis is y axis in the embodiments of the present disclosure.

Figure 2:
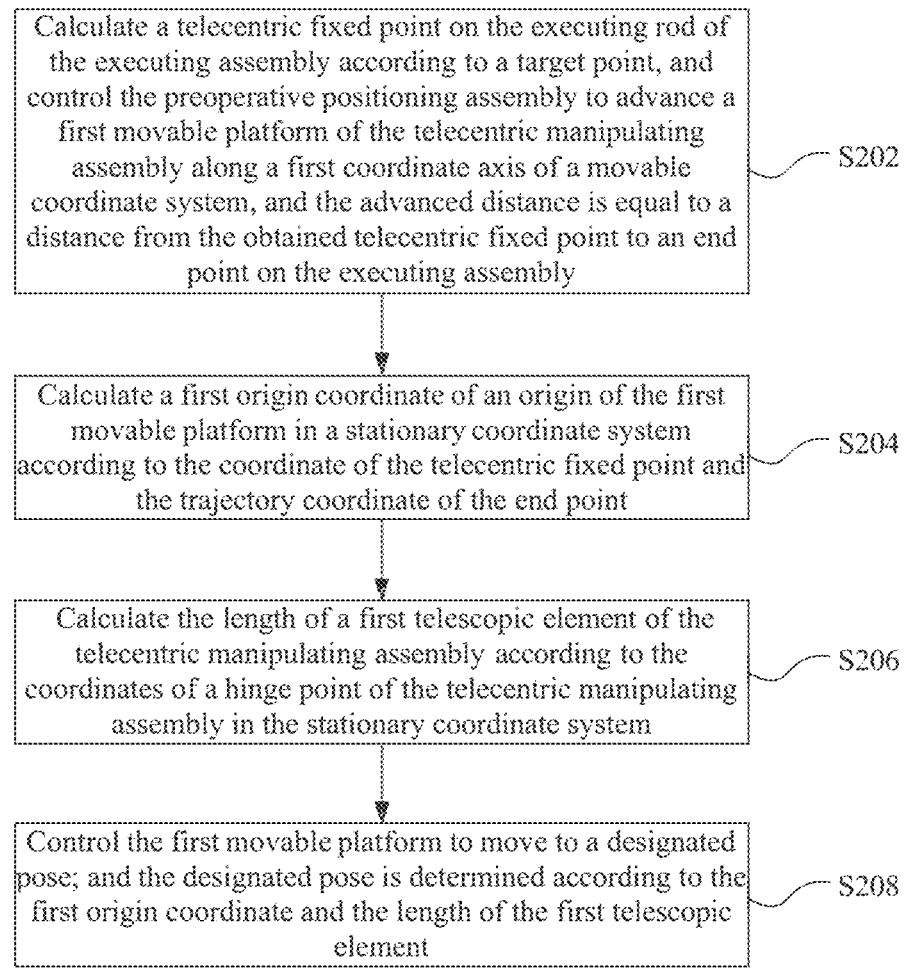
FIG. 2 is a flow diagram of a control method of a surgical robotic arm according to one embodiment of the present disclosure.

In the present embodiment, a control method for a surgical robotic arm is provided. FIG. 2 is a flow diagram of a control method for a surgical robotic arm according to one embodiment of the present disclosure, as illustrated in FIG. 2, the method includes:

in step S202, calculating a telecentric fixed point on the executing rod 1424 according to a target point, particularly, the target point is provided by an operator, the position of the target point is provided by the position of a doctor's main manipulator, and the position of the telecentric fixed point on the executing rod 1424 is obtained by calculating the distance between the target point position and the minimally invasive opening.

The preoperative positioning assembly 12 is controlled to advance the first movable platform 1446 of the telecentric manipulating assembly 144 along the first coordinate axis of the movable coordinate system, and the advanced distance is obtained through a ranging sensor, the advanced distance is equal to the distance between the telecentric manipulating assembly 144 and the end point obtained according to the coordinates, and the ranging sensor is set at the connection between the executing rod 1424 and the telecentric manipulating assembly 144; in addition, during the advanced process, the active arm 14 may be brought by the preoperative positioning assembly 12 to move so that the telecentric fixed point coincides with the minimally invasive opening; or, the active arm 14 may be brought by the preoperative positioning assembly 12 to move to a designated position, and moved by the telecentric manipulating assembly 144 along the first coordinate axis, so that the telecentric fixed point coincides with the minimally invasive opening, thereby improving accuracy of the coincidence process. The telecentric manipulating assembly 144 may be a Stewart parallel platform.

FIG. 3A is an axial view of a telecentric manipulating assembly according to embodiments of the present disclosure; FIG. 3B is a front view of a telecentric manipulating assembly according to embodiments of the present disclosure; and FIG. 3C is a top view of a telecentric manipulating assembly according to embodiments of the present disclosure, as illustrated in FIGS. 3A to 3C, the telecentric manipulating assembly 144 includes a first movable platform 1446, a static platform 1442, a movable hinge pair, a static hinge pair and a first telescopic element 1444, and the telecentric manipulating assembly 144 is connected with the executing rod 1424. A movable hinge point on the platform is a connection point thereof on the first movable platform 1446, and a static hinge point is a connection point thereof on the static platform 1442, and six static hinge points $S_1$, $S_2$, $S_3$, $S_4$, $S_5$ and $S_6$ are distributed circumferentially on the static platform 1442, and six movable hinge points $M_1$, $M_2$, $M_3$, $M_4$, $M_5$ and $M_6$ are distributed circumferentially on the first movable platform 1446; the center angle corresponding to the nearest adjacent movable hinge points is $\alpha$, and the center angle corresponding to the nearest adjacent static hinge points is $\beta$; the radius of the first movable platform 1446 is $r_S$, and the radius of the static platform 1442 is $r_M$.

At an initial time, the executing rod 1424 is perpendicular to the first movable platform 1446, and the axis of the executing rod 1424 passes through the center of the telecentric manipulating assembly 144, and $l_h$ is the distance from the end point T of the executing rod 1424 to the telecentric fixed point F; lj is the part where the executing rod 1424 coincides with the telecentric fixed point during the platform movement, where $F_1$ and $F_2$ are the two end points of this part on the executing rod 1424; h is a perpendicular distance between the first movable platform 1446 and the static platform 1442 at the initial time; and l is the length of the executing rod 1424.

Respective coordinate systems of the telecentric manipulating assembly 144 are established as follows: the stationary coordinate system $O_S$-$X_S Y_S Z_S$ is fixedly connected to the static platform 1442, the origin is established at the center $O_S$ of the static hinge distribution circle during the initial pose (i.e. the pose shown in FIG. 3), the $X_S$ axis is along an angular bisector of an angle $S_5 O_S S_6$, the $Z_S$ axis is perpendicular to the static platform 1442 and upward, and the $Y_s$ axis conforms to the right-hand rule; the movable coordinate system $O_M$-$X_M Y_M Z_M$ is fixedly connected to the first movable platform 1446, the origin is established at the circle center OM of the movable hinge point distribution circle in the initial position, and each axis is parallel to the corresponding axis of the static coordinate system during the initial pose. The static hinge coordinate system $S_i$-$X_{Si} Y_{Si} Z_{Si}$ (i=1, 2, 3 . . . 6) is fixedly connected to the static platform 1442, the origin is located at the center of the static hinge point of the corresponding reference sign, the $X_{Si}$ axis points to $S_i$ from the center $O_S$ of the static hinge point distribution circle, the $Z_{Si}$ axis is perpendicular to the static platform 1442 and upward, and $Y_{si}$ conforms to the right-hand rule ($S_4$-$X_{S4} Y_{S4} Z_{S4}$ is shown in FIG. 3); the movable hinge coordinate system $M_i$-$X_{Mi} Y_{Mi} Z_{Mi}$ is fixedly connected to the first movable platform 1446, the origin is located at the center of the movable hinge point of the corresponding reference sign, the $X_{Mi}$ axis points to $M_i$ from the center OM of the static hinge point distribution circle, the $Z_{Mi}$ axis is perpendicular to the static platform 1442 and upward, and $Y_{Mi}$ conforms to the right-hand rule.

Parameters of the size of the telecentric manipulating assembly 144 are illustrated as Table 1, thereby obtaining a first coordinate ($f_x$, $f_y$, $f_z$) of the telecentric fixed point in the stationary coordinate system $O_S$-$X_S Y_S Z_S$.

TABLE 1

Parameters of the Size of the Telecentric Manipulating Assembly

| | |
|---|---|
| Radius of the static hinge point distribution circle $r_s$ | 70 mm |
| Minimum included angle of the static platform hinge point $\alpha$ | 45° |
| Perpendicular distance between the movable platform and the static platform h | 160 mm |
| Distance from an end to $F_1$ $l_h$ | 100 mm |
| Radius of the movable hinge point distribution circle $r_m$ | 40 mm |
| Minimum included angle of the first movable platform hinge point $\beta$ | 45° |
| Length of the executing rod l | 350 mm |
| Coincidence range of the executing rod and the telecentric point $l_j$ | 100 mm |

In addition, during the operation, the executing assembly 142 always moves around the telecentric fixed point coincident with the patient's minimally invasive opening and performs the surgical operation; in order to realize the swing of the surgical instrument 1426 in the surgical robotic arm in different areas, the telecentric fixed point on the executing rod 1424 may move within a preset range, according to FIG. 3A and Table 1, the preset range is a range between $F_1$ and $F_2$ points on the executing rod 1424, and in the embodiments of the present disclosure, the length of the range is 100 mm.

In step S204, in the case where the first coordinate system is unchanged, a first origin coordinate of an origin of the first movable platform 1446 in a stationary coordinate system is calculated according to the coordinate of the telecentric fixed point and the trajectory coordinate of the end point on the executing rod 1424;

The coordinate of the telecentric fixed point F in the stationary coordinate system is ($f_x$, $f_y$, $f_z$), and $f_x=f_y=0$, $f_z=h+1-l_h$. The trajectory point at the end of the surgical robot is given according to the control system, so that the trajectory point T at any time is known to be expressed as ($t_x$, $t_y$, $t_z$). After the entire platform is pushed forward to the corresponding position by the preoperative positioning assembly 12 at the rear end (at this time, the end of the executing rod 1424 has been extended into the body), the telecentric fixed point F (0, 0, h+1-$l_h$) coincides with $F_1$ on the executing rod 1424. At this time, the coordinate of the end point in an absolute coordinate system is (0, 0, h+1). During the movement, the first movable platform 1446 moves according to the predetermined requirements in the stationary coordinate system, which may be converted into taking the movable coordinate system as the benchmark, and the telecentric fixed point F fixed in the stationary coordinate system moves within the range between $F_1$ and $F_2$ on the executing rod 1424. Therefore, the movement range of the first movable platform 1446 in the $Z_S$ direction is $l_j$, the movement range of the corresponding surgical instrument 1426 in the $Z_S$ direction is also $l_j$, and the coordinate range of the end in the corresponding direction is $t_z \in$[h+1, h+1+lj].

In step S206, the length of the first telescopic element 1444 of the telecentric manipulating assembly 144 is calculated according to the coordinate of the movable hinge point in the stationary coordinate system and the coordinate of the static hinge point in the stationary coordinate system; and a distance between any pair of movable and static hinge points is calculated according to the distance formula between two points in space, as illustrated in Formula 1:

$$l_i = \sqrt{(sm_{ix}-ss_{ix})^2 + (sm_{iy}-ss_{iy})^2 + (sm_{iz}-ss_{iz})^2} \quad \text{Formula 1}$$

In step S208, the first movable platform 1446 is controlled to move to the designated pose; and the designated pose is determined according to the origin coordinate and the length of the first telescopic element 1444; when it is necessary to adjust to the designated pose, the first movable platform 1446 is moved according to the origin coordinate and the length of the first telescopic element 1444, and the first movable platform 1446 adjusts the executing rod 1424 to deflect a certain angle around the telecentric fixed point, and the six first telescopic elements 1444 are kept uniformly adjusted during the adjustment.

In related technologies, the surgical robot usually has a large range of motion during the surgical process. However, in the embodiments of the present disclosure, through the above steps S202 to S208, the telecentric fixed point on the executing rod 1424 is calculated according to the target point, and real time inverse solution is performed according to the telecentric fixed point and the end trajectory of the executing rod 1424 to obtain the pose of the first movable platform 1446, thereby easily realizing online real-time calculation of the inverse solution, and ensuring that the executing rod 1424 has a certain telecentric fixed point when it is deflected at different angles, so as to keep the skin wound not to be cut by the approaching executing rod 1424 during the operation. Furthermore, compared with the related technologies, the structure of Da Vinci surgical robot is complex with expensive cost, and its service life is limited due to load. In this case, Da Vinci's use of parallelogram structure brings interference problems. A parallel mechanism formed through the connection of the first movable platform 1446 and the static platform 1442 and its control method in the embodiments of the present disclosure have a simpler structure and a smaller structural size with a larger bearing capacity, thereby solving the problems of large structural size of the surgical robotic arm and interference between the surgical robotic arms and reducing the cost.

Figure 4:
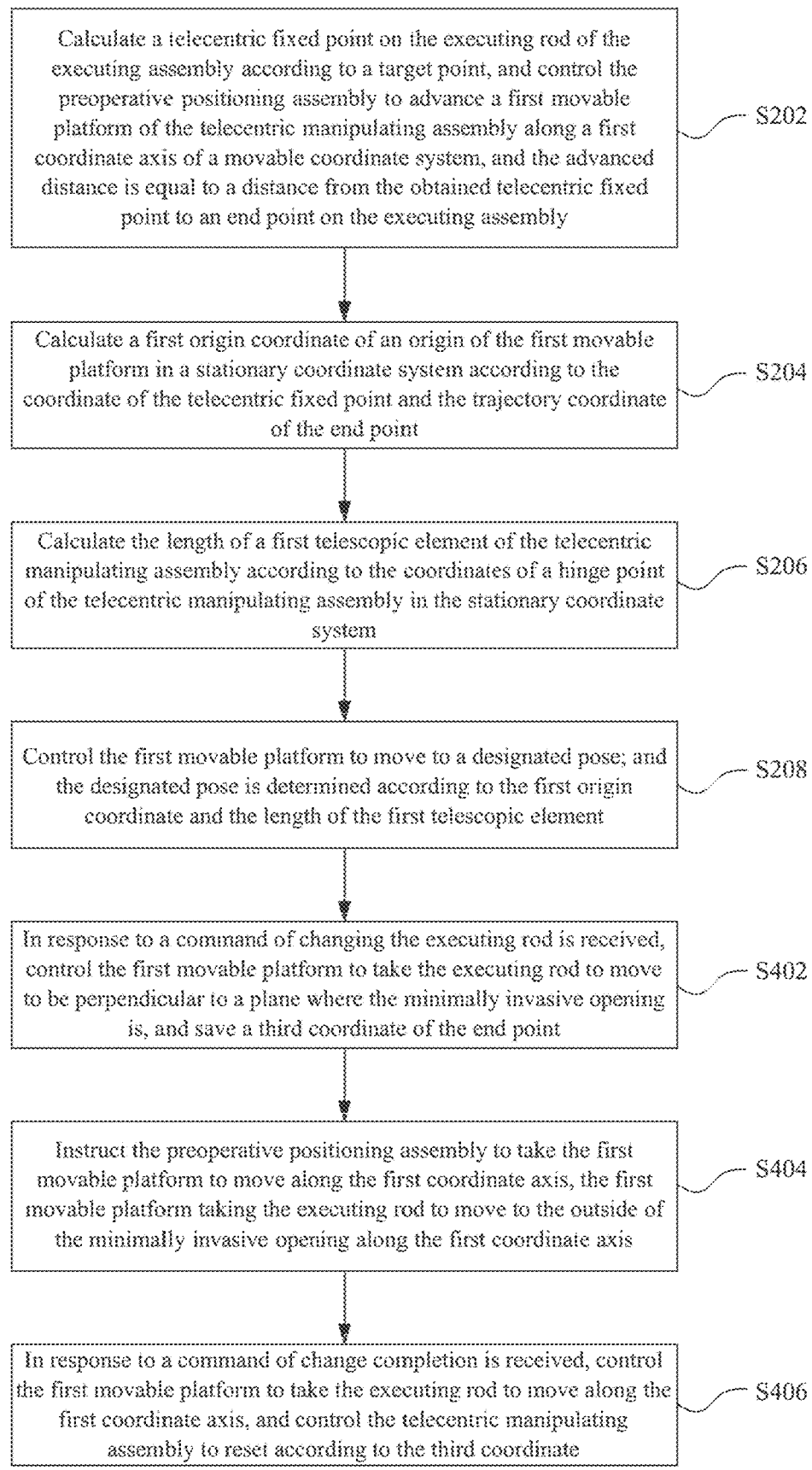
FIG. 4 is a flow diagram of a control method of a surgical robotic arm according to another embodiment of the present disclosure.

In one embodiment, a control method for a surgical robotic arm is provided. FIG. 4 is a flow diagram of a control method for a surgical robotic arm according to one embodiment of the present disclosure, as illustrated in FIG. 4, the method further includes:

in step S402, in response to a command of changing the executing rod 1424 is received, controlling the first movable platform 1446 to take the executing rod 1424 to move to be perpendicular to a plane where the minimally invasive opening is, and saving a third coordinate of the telecentric fixed point; for example, in the case of biopsy sampling or ablation resection of lesions for different purposes, different executing rods 1424 need to be used to achieve the corresponding purpose. After receiving the command of changing the executing rod 1424, the control system first calculates the coordinate in the movable coordinate system of an end point that is the same as the coordinate of the telecentric fixed point in the x axis and y axis directions according to the coordinate of the telecentric fixed point. The first movable platform is moved according to the coordinates of the telecentric fixed point and the end point, so that the executing rod 1424 is perpendicular to the plane where the minimally invasive opening is, and the end point coordinate at this time, that is, a first coordinate, is saved, for subsequent operations to take out of the executing rod 1424 from the patient's body;

in step S404, ensuring to lock in the x axis and y axis directions and instructing the preoperative positioning assembly to take the first movable platform to move along the first coordinate axis, that is, y axis, and the first movable platform 1446 takes the executing rod to move to the outside of the minimally invasive opening along the first coordinate axis, thereby controlling the executing rod 1424 to be taken out of the patient's body along the z axis direction;

in step S406, in response to a command of change completion is received, controlling the first movable platform 1446 to take the executing rod 1424 to move along the first coordinate axis, and resetting the telecentric fixed point to coincide with the minimally invasive opening according to the third coordinate; and when the change of the executing rod 1424 has been completed, the control system receives the command of change completion, controls the executing rod 1424 to reset, and continues the operation.

Through the above steps S402 to S404, in response to the command of changing the executing rod 1424 is received, the first movable platform 1446 is controlled to move along the first coordinate axis, and the first movable platform 1446 takes the executing rod 1424 to move to the outside of the minimally invasive opening along the first coordinate axis, thereby ensuring the minimally invasive opening not to be expanded when the executing rod 1424 is changed.

Figure 5:
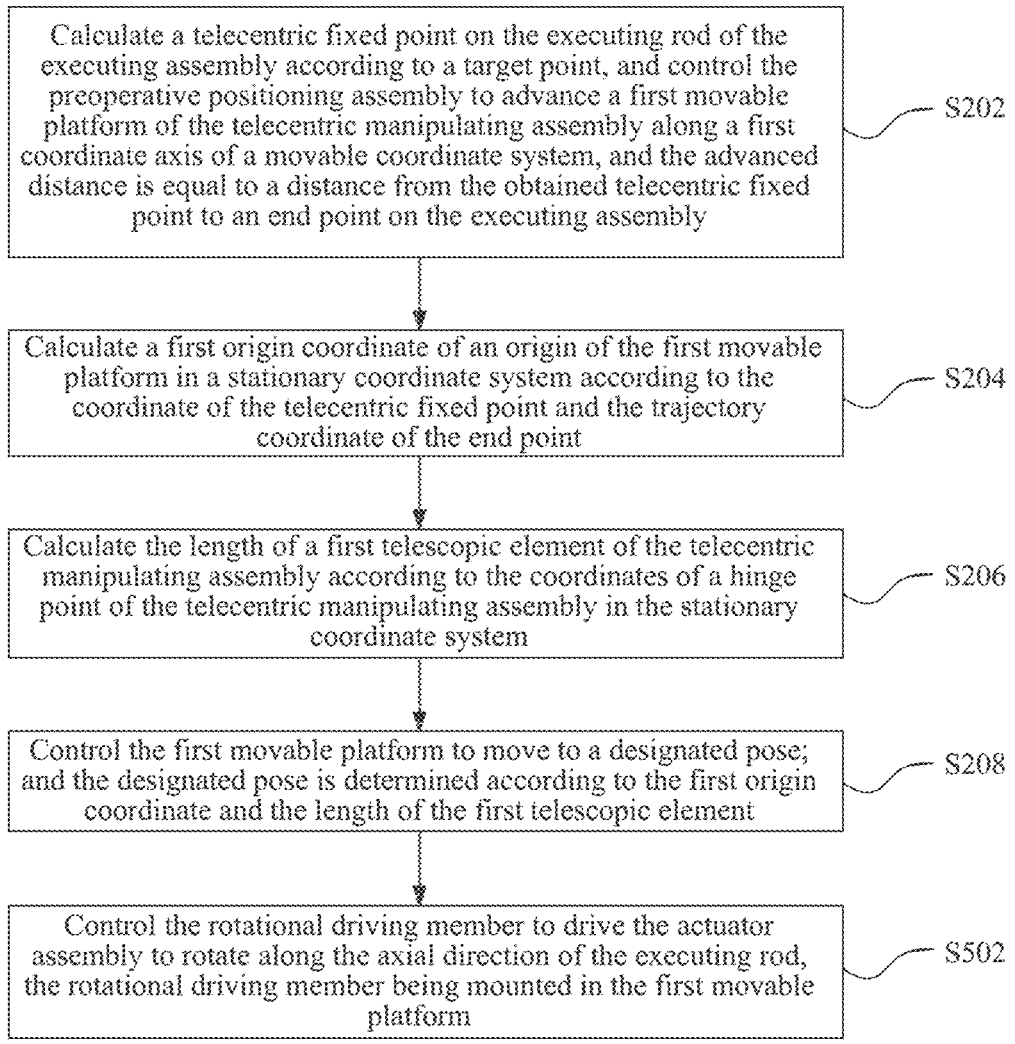
FIG. 5 is a flow diagram of a control method of a surgical robotic arm according to another embodiment of the present disclosure.

In one embodiment, a control method for a surgical robotic arm is provided. FIG. 5 is a flow diagram of a control method for a surgical robotic arm according to another embodiment of the present disclosure, as illustrated in FIG. 5, the method further includes:

in step S502, when the driving member 1422 includes a rotational driving member, a first deflection driving member, a second deflection driving member and an opening and closing driving member, controlling the rotational driving member to drive the actuator assembly 142 to rotate along the axial direction of the executing rod 1424, the rotational driving member being mounted in the first movable platform 1446.

Furthermore, the first deflection driving member, the second deflection driving member and the opening and closing driving member are mounted at the connection between the executing assembly 142 and the first movable platform 1446, the first deflection driving member and the second deflection driving member drive the built-in transmission cable of the executing assembly to bring the surgical instrument 1426 of the executing assembly to deflect toward two staggered different directions, respectively, and the opening and closing driving member brings the surgical instrument 1426 to open and close through the transmission cable.

Through the above step S502, the rotational driving member that drives the executing rod 1424 and the surgical instrument 1426 to rotate synchronously along the axial direction of the executing rod 1424 is mounted in the first movable platform 1446, which avoids occurrence of distortion of the steel wire rope when all of the four motors are placed at one end of the executing rod 1424 and rotate along the z axis, thereby further improving the surgical accuracy, reducing the output power of the driving member 1422 and increasing the service life of the driving member 1422.

In one embodiment, a control method for a surgical robotic arm is provided, and the telecentric manipulating assembly of the surgical robotic arm in this embodiment also includes a multi-level interconnected parallel platform; it should be additionally explained that each level parallel platforms may include two platforms and telescopic elements between the two platforms. For example, the first level parallel platforms include two platforms, namely, the first movable platform 1446 and the static platform 1442; the second level parallel platforms may also include two platforms, namely, the second movable platform and the installation platform fixed on the first movable platform 1446 (not shown in the figure).

As it should be, in addition to the two platforms required for the first level parallel platforms, the corresponding installation platforms may also be omitted for the second level parallel platforms and larger level parallel platforms, and it is assumed by certain one of the previous level parallel platforms. For example, the second level parallel platforms include two platforms, namely, the second movable platform and the first movable platform 1446 in the first level parallel platforms, that is, the first movable platform 1446 is shared by two levels of parallel platforms in this case.

To sum up, "each level parallel platforms include two opposite platforms and telescopic elements between the two platforms" mentioned in the present disclosure has two cases: one is that each level parallel platform has two platforms, and the two platforms are not shared among different level parallel platforms; and one is that each level parallel platforms implement its own relative movement between two platforms by sharing the adjacent level platforms.

Figure 6:
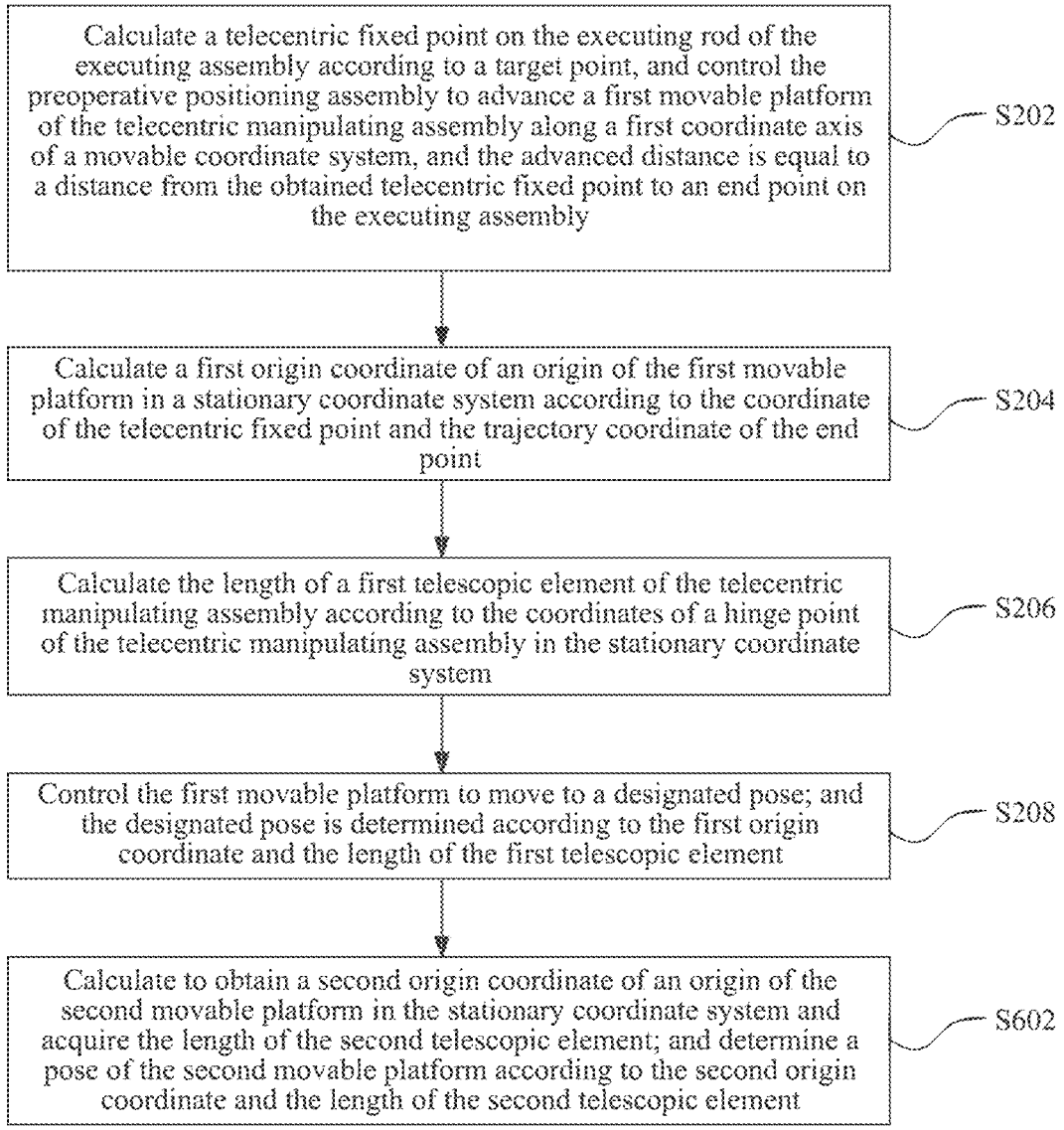
FIG. 6 is a flow diagram of a control method of a surgical robotic arm according to another embodiment of the present disclosure.
Figure 7A:
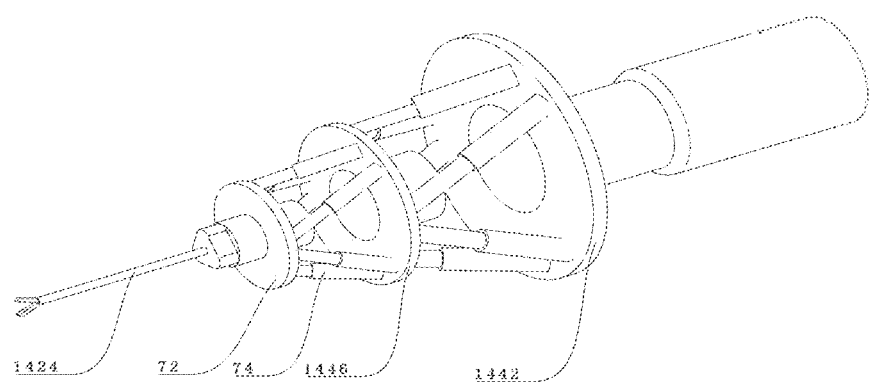
FIG. 7A is a stereogram of a telecentric manipulating assembly according to embodiments of the present disclosure.

Particularly, the number of levels of the parallel platforms is two. That is, the telecentric manipulating assembly 144 further includes second level parallel platforms connected to the first level parallel platforms, and the second level parallel platforms include a second movable platform and a plurality of second telescopic elements disposed between the first movable platform 1446 and the second movable platform; and one side of the second movable platform relatively far away from the static platform 1442 of the telecentric manipulating assembly 144 is fixedly connected to the executing assembly 142; FIG. 6 is a flow diagram of a control method for a surgical robotic arm according to another embodiment of the present disclosure, as illustrated in FIG. 6, the method further includes:

in step S602, calculating to obtain a second level origin coordinate of the origin of the second movable platform in the stationary coordinate system and acquire the length of the second telescopic element; and FIG. 7A is a stereogram of a telecentric manipulating assembly according to embodiments of the present disclosure; as illustrated in FIG. 7A, the second movable platform 72 and a plurality of second telescopic elements 74 disposed between the first movable platform 1446 and the second movable platform 72, and the second movable platform 72 is connected to the executing assembly 142.

Figure 7B:
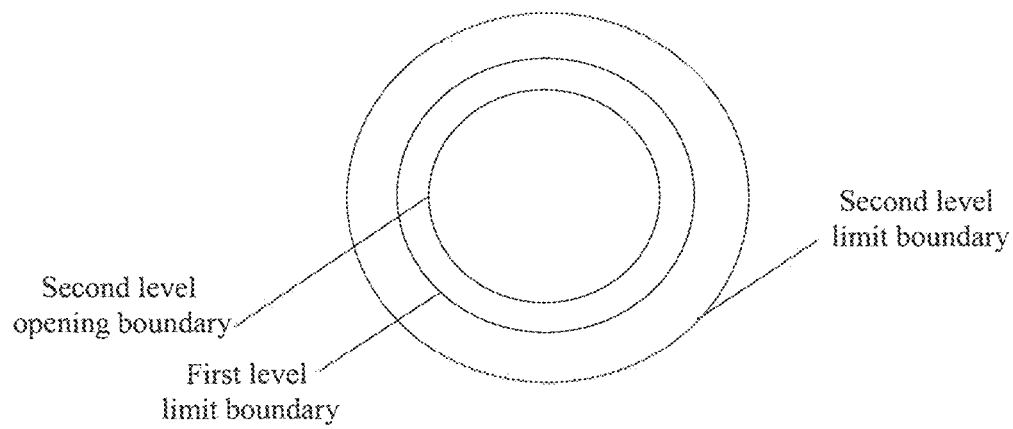
FIG. 7B is a top view of a telecentric manipulating assembly according to embodiments of the present disclosure.

FIG. 7B is a top view of a telecentric manipulating assembly according to embodiments of the present disclosure; as illustrated in FIG. 7B, a deflection angle movement range of the first movable platform 1446 of the first level is within the limit boundary of the first level; when the telecentric manipulating assembly 144 moves within the second level opening boundary, the second movable platform 72 is in the zero position and locked state; once the calculated deflection angle of the first movable platform 1446 exceeds the second level opening boundary, the second level is unlocked for movement, and the moving boundary after starting the second level platform is a second level limit boundary. In this case, the motion of the first movable platform 1446 is limited to the first level limit boundary, and the plane formed by the normal of the deflection angle of the second movable platform 72 and the telecentric fixed point is ensured to be in the same plane as the plane formed by the normal of the deflection of the first movable platform 1446 and the telecentric fixed point, thereby preventing the telecentric manipulating assembly 144 from being in a distorted state; and the circular area between the first level limit boundary and the second level limit boundary in FIG. B is a safety control area, and the set value of the safety control area may be greater than the possible maximum deflection angle of the first movable platform 1446 within a single movement command cycle (e.g. 1 ms), for example, the maximum deflection angle is 1°.

When the telecentric manipulating assembly enters the area within the second level opening boundary, the second movable platform moves to the zero position, and furthermore the first level movable platform 1446 moves to the target value; and the first and second level movements may satisfy the original fixed point constraint conditions.

The pose of the second movable platform 72 is determined according to the second level origin coordinate and the length of the second telescopic element 74; and the algorithm for the second level origin coordinates is the same as that for the origin coordinate, and the algorithm for the length of the second telescopic element 74 is the same as that for the length of the first telescopic element 1444.

Through the above step S602, the pose of the second movable platform is determined by adding a second movable platform and according to the second level origin coordinate and the length of the second level first telescopic element, which implements the multi-level solutions of the surgical robotic arm, since the deflection angle of the single level Stewart parallel mechanism is small, the single level platform is superimposed into multi-level platforms, which may accumulate the deflection angles, thereby increasing the surgical space of the surgical instrument 1426.

In one embodiment, a control method for a surgical robotic arm is provided, and the method further includes:

in step S702, determining a first calculation model according to the relationship among the coordinate of the telecentric fixed point, the trajectory coordinate and a direction vector module length, the direction vector module length being a direction vector module length of the executing rod 1424 in the stationary coordinate system; determining a second calculation model according to a positional relationship among the coordinate of the telecentric fixed point, the trajectory coordinate and the first origin coordinate; determining a third calculation model according to a distance formula between the trajectory coordinate and the origin coordinate; and obtaining the origin coordinate according to the first calculation model, second calculation model and the third calculation model;

and at any time, the coordinate of the telecentric fixed point is (fx, fy, fz), and the trajectory coordinate of the end point is (tx, ty, tz), and since the coordinate of the telecentric fixed point and the trajectory coordinate are located on the executing rod 1424, the direction vector of the straight line where the executing rod 1424 is located in the stationary coordinate system is obtained as:

$$\underline{D} = [t_x - f_x, t_y - f_y, t_z - f_z] \qquad \text{Formula 2}$$

The module length of the direction vector is calculated to obtain the first calculation model, as illustrated in Formula 3:

$$r_{tf} = \sqrt{(t_x - f_x)^2 + (t_y - f_y)^2 + (t_z - f_z)^2} \quad \text{Formula 3}$$

According to the definition, the origin of the movable coordinate system $O_M = (m_{ox}, m_{oy}, m_{oz})$ is at the center of the plane where the movable hinge point is, thus, the telecentric fixed point coordinate, the trajectory coordinate and the origin coordinate at any time are on the same one straight line, meeting the following relationship:

$$\frac{t_x - f_x}{t_x - m_{ox}} = \frac{t_y - f_y}{t_y - m_{oy}} = \frac{t_z - f_z}{t_z - m_{oz}} = k \quad \text{Formula 4}$$

Since the end point and the telecentric fixed point do not coincide, that is, k≠0.

The above Formula 4 may be converted into a second calculation model, as illustrated in Formula 5:

$$\frac{t_i - f_i}{k} = t_i - m_{oi} \quad \text{Formula 5}$$

where i is x, y, z. Considering that the distance between the end point and the movable coordinate system origin is a fixed value, that is, the length of the executing rod 1424 is 1, a third calculation model may be obtained, as illustrated in Formula 6:

$$(t_x - m_{ox})^2 + (t_y - m_{oy})^2 + (t_z - m_{oz})^2 = l^2 \quad \text{Formula 6}$$

According to the first calculation model again, there is:

$$\left(\frac{t_x - f_x}{k}\right)^2 + \left(\frac{t_y - f_y}{k}\right)^2 + \left(\frac{t_z - f_z}{k}\right)^2 = \frac{r_{tf}^2}{k^2} \quad \text{Formula 7}$$

Combining Formula 5, Formula 6 and Formula 7, k may be expressed by the coordinates of the telecentric point and the end point in the stationary coordinate system, thereby obtaining the coordinate of the movable coordinate system origin OM in the stationary coordinate system.

Through the above step S702, the first calculation model, the second calculation model and the third calculation model are determined through the telecentric fixed point and the end movement trajectory of the executing rod 1424; and the origin coordinate is calculated according to the first calculation model, the second calculation model and the third calculation model, thereby implementing real time determination of the movement trajectory of the first movable platform 1446 during the operation, and improving the operation accuracy.

In one embodiment, a control method for a surgical robotic arm is provided, and the method further includes:

in step S802, determining a first transformation matrix according to a first rotational angle and a second rotational angle; and the first rotational angle is an angle that the executing rod 1424 rotates about a second coordinate axis, and the second rotational angle is an angle that the executing rod 1424 rotates about a third coordinate axis; the second coordinate axis may be X axis, and the third coordinate axis may be Y axis.

For the executing rod 1424, the rotational movement thereof may be described as rotating around XM and YM coordinate axes in the movable coordinate system successively during the operation, where the first rotational angle is $\lambda_x$ and the second rotational angle is $\lambda_y$, and the first transformation matrix is:

$$^SR_M = \begin{bmatrix} 1 & 0 & 0 \\ 0 & \cos(\lambda_x) & -\sin(\lambda_x) \\ 0 & \sin(\lambda_x) & \cos(\lambda_x) \end{bmatrix} \begin{bmatrix} \cos(\lambda_y) & 0 & \sin(\lambda_y) \\ 0 & 1 & 0 \\ -\sin(\lambda_y) & 0 & \cos(\lambda_y) \end{bmatrix} \quad \text{Formula 8}$$

$$= \begin{bmatrix} \cos(\lambda_y) & 0 & \sin(\lambda_y) \\ \sin(\lambda_y)\sin(\lambda_x) & \cos(\lambda_x) & -\sin(\lambda_x)\cos(\lambda_y) \\ -\cos(\lambda_x)\sin(\lambda_y)) & \sin(\lambda_y) & \cos(\lambda_y)\cos(\lambda_s) \end{bmatrix}$$

The vector from F to T coincides with the ZM axis in the movable coordinate system, which may be expressed as $\vec{Z_m} = [0, 0, \text{rtf}]$, and the transformation relationship of the vector in the two coordinate systems is expressed as in Formula 9:

$$\vec{D} = {}^SR_M \times \vec{Z_m}^T \quad \text{Formula 9}$$

The direction vectors $\vec{Z_m}$ and Formula 9 are substituted into Formula 8 to obtain the calculation formula shown in Formula 10:

$$\begin{bmatrix} t_x - f_x \\ t_y - f_y \\ t_y - f_y \end{bmatrix} = \begin{bmatrix} \cos(\lambda_y) & 0 & \sin(\lambda_y) \\ \sin(\lambda_y)\sin(\lambda_x) & \cos(\lambda_x) & -\sin(\lambda_x)\cos(\lambda_y) \\ -\cos(\lambda_x)\sin(\lambda_y)) & \sin(\lambda_y) & \cos(\lambda_y)\cos(\lambda_x) \end{bmatrix} \begin{bmatrix} 0 \\ 0 \\ r_{tf} \end{bmatrix} \quad \text{Formula 10}$$

During the operation, x∈(−90°, 90), y∈(−90°, 90), and the sine functions of x and y increase monotonically within the range. Inspecting that a first element in the third column of the first transformation matrix may obtain an Euler angle $\lambda_y$ rotating around the $Y_M$ axis by using the inverse sine function, similarly, the Euler angle $\lambda_x$ rotating around the $X_M$ axis may be obtained by combining a second element in the third column of the first transformation matrix also, and the first transformation matrix may be uniquely determined and obtained.

In step S804, the first coordinate is determined according to the first transformation matrix, and the length of the first telescopic element 1444 of the telecentric manipulating assembly 144 is calculated according to the first coordinate and the second coordinate; and the coordinate of any static hinge point Si in the stationary coordinate system is ($ss_{ix}$, $ss_{iy}$, 0), and the coordinate of the corresponding movable hinge point $M_i$ thereof in the movable coordinate system may be expressed as ($mm_{ix}$, $mm_{iy}$, 0), and the calculation formula of the coordinate thereof in the stationary coordinate system $^SM_i = (sm_{ix}, sm_{iy}, 0)$ is:

$$^SM_i = {}^SR_M M_i \quad \text{Formula 11}$$

The first and second coordinates are substituted into Formula 1 to calculate the distance between any pair of movable and static hinge points, that is, the length $l_i$ of the first telescopic element 1444;

in order to meet the elongation condition of the first telescopic element 1444, the rod length at any time meets the following formula:

$$l_{min} \leq l_i \leq l_{max} \quad \text{Formula 12}$$

Through the above steps S802 to S804, according to the coordinate of the movable hinge point in the stationary coordinate system and the coordinate of the static hinge point in the stationary coordinate system, the length of the first telescopic element 1444 is calculated by using the distance formula of two points in space, thereby inversely solving the pose of the first movable platform 1446 during the operation, and improving the response speed to the control system command.

In one embodiment, a control method for a surgical robotic arm is provided, and the method further includes:
  in step S902, acquiring a first homogeneous coordinate of the movable hinge point in the movable coordinate system according to the first origin coordinate and the third rotational angle; acquiring a second homogeneous coordinate of the static hinge point in the stationary coordinate system according to the first origin coordinate and the fourth rotational angle, and the third rotational angle is an angle that the movable hinge point rotates about the origin of the first movable platform 1446, and the fourth rotational angle is an angle that the static hinge point rotates about the origin of the static platform 1442;
  and now calculating the coordinate of the movable hinge point in the movable coordinate system and the coordinate of the static hinge point in the stationary coordinate system. Taking calculation of the static hinge point as an example, as previously said, first, the static hinge point $S_i$ (i=1~6) is moved from the stationary coordinate system origin $O_S$ to the intersection of the axis of the stationary coordinate system $X_S$ and the distribution circle of the stationary coordinate system platform, the coordinate value at this time is ($r_s$,0). According to the plane coordinate rotation theorem, the coordinate of any coordinate point (x, y) after rotating an angle θ around the origin may be obtained by calculating formula 13:

$$x' = x \cos\theta - y \sin\theta, y' = x \sin\theta + y \cos\theta \qquad \text{Formula 13}$$

The coordinate ($r_s$,0) as the values of x and y is substituted into Formula 13, and the coordinate thereof may be expressed as:

$$(ss_{ix}, ss_{iy}) = (r_s \cos\theta_{si}, r_s \sin\theta_{si}) \qquad \text{Formula 14}$$

and $s_i$ is a rotational angle of rotating from the intersection to the corresponding hinge point with the stationary coordinate system origin as the center of the circle.

The static platform 1442 coordinate system origin is defined at the center of the plane where the static hinge point is, therefore, the $Z_S$ axial coordinate of any static hinge point in the static coordinate system is 0, furthermore, considering the coordinate rotation and translation transformation, the second homogeneous coordinate of the static hinge point in the static platform 1442 may be obtained:

$$S_i = (ss_{ix}, ss_{iy}, 0, 1) \qquad \text{Formula 15}$$

The rotational angle during the transformation of the corresponding hinge point is given by Table 2.

TABLE 2

Corresponding Transformation Rotational Angle of Static Hinge Point

| Hinge Point | $S_1$ | $S_2$ | $S_3$ | $S_4$ | $S_5$ | $S_6$ |
|---|---|---|---|---|---|---|
| Angle Value $\theta_i$ | $\frac{\pi}{3}+\frac{\alpha}{2}$ | $\pi-\frac{\alpha}{2}$ | $\pi+\frac{\alpha}{2}$ | $\frac{5\pi}{3}-\frac{\alpha}{2}$ | $\frac{5\pi}{3}+\frac{\alpha}{2}$ | $\frac{\pi}{3}-\frac{\alpha}{2}$ |

Similarly, the first homogeneous coordinate of the movable hinge point in the movable coordinate system is obtained:

$$M_i = (mm_{ix}, mm_{iy}, 0, 1) \qquad \text{Formula 16}$$

The rotational angle during the transformation of the corresponding hinge point is given by Table 3.

TABLE 3

Corresponding Transformation Rotational Angle of Movable Hinge Point

| Hinge Point | $M_1$ | $M_2$ | $M_3$ | $M_4$ | $M_5$ | $M_6$ |
|---|---|---|---|---|---|---|
| Angle Value $\theta_i$ | $\frac{2\pi}{3}-\frac{\beta}{2}$ | $\frac{2\pi}{3}+\frac{\beta}{2}$ | $\frac{4\pi}{3}-\frac{\beta}{2}$ | $\frac{4\pi}{3}+\frac{\beta}{2}$ | $-\frac{\beta}{2}$ | $\frac{\beta}{2}$ |

In step S904, a second transformation matrix is determined according to the first transformation matrix and the origin coordinate, and a third homogeneous coordinate of the movable hinge point in the stationary coordinate system is obtained according to the second transformation matrix and the first homogeneous coordinate;

For facilitating coordinate transformation, the second transformation matrix defined from the static coordinate S to the movable coordinate M may be expressed as:

$$^S T_M = \begin{bmatrix} \cos(\lambda_y) & 0 & \sin(\lambda_y) & m_{ox} \\ \sin(\lambda_y)\sin(\lambda_x) & \cos(\lambda_x) & -\sin(\lambda_x)\cos(\lambda_y) & m_{oy} \\ -\cos(\lambda_x)\sin(\lambda_y) & \sin(\lambda_y) & \cos(\lambda_y)\cos(\lambda_x) & m_{oz} \\ 0 & 0 & 0 & 1 \end{bmatrix} \qquad \text{Formula 17}$$

The homogeneous coordinate of any static hinge point Si in the stationary coordinate system is ($ss_{ix}$, $ss_{iy}$, 0, 1), and the homogeneous coordinate of the corresponding movable hinge point $M_i$ thereof in the movable coordinate system may be expressed as ($mm_{ix}$, $mm_{iy}$, 0, 1), and the calculation formula of the third homogeneous coordinate $SM_i = (sm_{ix}, sm_{iy}, 0, 1)$ thereof in the stationary coordinate system is:

$$^S M_i = {}^S T_M M_i \qquad \text{Formula 18}$$

In step S906, the length of the first telescopic element 1444 of the telecentric manipulating assembly 144 is calculated according to the second homogeneous coordinate and the third homogeneous coordinate; and the second homogeneous coordinate is the homogeneous coordinate of the static hinge point in the stationary coordinate system; the second homogeneous coordinate and the third homogeneous coordinate are substituted into Formula 12, and the length of the first telescopic element 1444 may be obtained.

Through the above steps S902 to s906, the homogeneous coordinate is determined through the second transformation matrix, compared with the determination of ordinary coordinates, the homogeneous coordinate is a four-dimensional vector, which itself contains pose information and position information, thereby obtaining the pose coordinate and position coordinate of the movable hinge point in the stationary coordinate system in one step, and further improving the response speed to the control system commands.

In one embodiment, a control method for a surgical robotic arm is provided, and the method further includes:
  in step S1002, when the telecentric fixed point is traversed from a first end point to a second end point, a first maximum value, a second maximum value and a third maximum value is calculated; and the first maximum value is the maximum value of the length of the first telescopic element 1444, the second maximum value is the maximum swing angle of the static hinge point and the third maximum value is the maximum swing angle of the movable hinge point;

and when the telecentric manipulating assembly 144 is in the initial position, the first telescopic element 1444 is near the shrinkage limit position. First, the homogeneous coordinate $^{S}M_{i0}=(sm_{ix0}, sm_{iy0}, sm_{iz0}, 1)$ of the movable hinge point in the stationary coordinate system in the initial position is calculated, $$sm_{ix0}=mm_{ix}, sm_{iy0}=mm_{iy}, sm_{iz0}=h \qquad \text{Formula 19}$$

thereby obtaining the direction vector of the first telescopic element 1444 in the stationary coordinate system in the initial position:

$$\overrightarrow{S_iM_i}=[sm_{ix0}-ss_{ix}, sm_{iy0}-ss_{iy}, sm_{iz0}-ss_{iz}] \qquad \text{Formula 20}$$

The coordinate of the movable hinge point in the stationary coordinate system is $^{S}M_i=(sm_{ix}, sm_{iy}, sm_{iz}, 1)$, and the vector pointing from the static hinge point to the movable hinge point in the stationary coordinate system at any time is:

$$\overrightarrow{S_iM_i'}=[sm_{ix}-ss_{ix}, sm_{iy}-ss_{iy}, sm_{iz}-ss_{iz}] \qquad \text{Formula 21}$$

i (i=1~6) is used to represent the static hinge swing angle, taking the fourth rod as an example, an included angle $\phi_4$ between the static hinge and the initial position of the first telescopic element 1444 at this time is:

$$\phi_4 = \arccos\left(\frac{\overrightarrow{S_4M_4} \cdot \overrightarrow{S_4M_4'}}{|\overrightarrow{S_4M_4}| \cdot |\overrightarrow{S_4M_4'}|}\right) \qquad \text{Formula 22}$$

In order to satisfy the requirement for the swing angle range, the limitation requirement for an included angle $\phi_i$ is:

$$0 \leq \phi_i \leq \phi_{imax} \qquad \text{Formula 23}$$

where $\phi_{imax}$ is a limit swing angle of ball hinge pair.

The above calculation process is solved through MATLAB to obtain the swing angle of the first telescopic element 1444 in the expected motion space, and under the existing parameter conditions, the minimum value of the maximum swing angle range of the static hinge (relative to the initial position) is about 22°. For the sake of safety, the maximum swing angle (in all directions relative to the initial position) of the selected ball hinge pair is ensured to be greater than or equal to 25°.

In order to calculate the swing angle at the movable hinge, the homogeneous coordinate $^{M}S_{i0}=(ms_{ix0}, ms_{iy0}, ms_{iz0}, 1)$ of the static hinge point in the movable coordinate system in the initial position is firstly calculated, as shown in Formula 24:

$$ms_{ix0}=ss_{ix}, ms_{iy0}=ss_{iy}, ms_{iz0}=-h \qquad \text{Formula 24}$$

thereby obtaining the direction vector of the first telescopic element 1444 in the movable coordinate system in the initial position, as shown in Formula 25:

$$\overrightarrow{M_iS_i}=[ms_{ix0}-mm_{ix}, ms_{iy0}-mm_{iy}, ms_{iz0}-mm_{iz}] \qquad \text{Formula 25}$$

the coordinate $^{M}S_i=(ms_{ix}, ms_{iy}, ms_{iz}, 1)$ of the static hinge point in the movable coordinate system may be known with the second transformation matrix, as shown in formula 26:

$$^{M}S_i=(^{S}T_M)^{-1}S_i \qquad \text{Formula 26}$$

where $S_i$ is a coordinate of the corresponding static hinge point in the stationary coordinate system. The vector pointing from the movable hinge point to the static hinge point in the movable coordinate system at any time is:

$$\overrightarrow{M_iS_i'}=[ms_{ix}-mm_{ix}, ms_{iy}-mm_{iy}, ms_{iz}-mm_{iz}] \qquad \text{Formula 27}$$

i (i=1~6) is used to represent the movable hinge swing angle. Taking the fourth rod as an example, an included angle $\varphi_4$ between the movable hinge and the initial position of the first telescopic element 1444 at this time is:

$$\varphi_4 = \arccos\left(\frac{\overrightarrow{M_4S_4} \cdot \overrightarrow{M_4S_4'}}{|\overrightarrow{M_4S_4}| \cdot |\overrightarrow{M_4S_4'}|}\right) \quad \varphi_4 \in \left[0, \frac{\pi}{2}\right] \qquad \text{Formula 28}$$

In order to satisfy the requirement for the swing angle range, the limitation requirement for an included angle i is:

$$0 \leq \varphi_i \leq \varphi_{imax} \qquad \text{Formula 29}$$

where $\varphi_{imax}$ is a Hooke hinge pair limit swing angle. The above calculation process is solved through MATLAB to obtain the swing angle at the Hooke hinge of the first telescopic element 1444 in the movable coordinate system. Under the existing parameter conditions, the minimum value of the maximum swing angle range of the movable hinge (relative to the initial position) is about 43°. For the sake of safety, the maximum swing angle (in all directions relative to the initial position) of the selected Hooke hinge pair is ensured to be greater than or equal to 45°.

And since the movement interference checking calculation of the hinge pair of the telecentric manipulating assembly 144 requires the specific size of each hinge pair member, some adjustable parameters (such as the size and perpendicular distance of the movable and static platforms, etc.) are first set, the parameters for the minimum required extension (route) of the rod length and the minimum movement swing angle of the hinge pair are optimized to obtain the recommended parameter values (the optimal condition to meet the requirements within the parameter range at this time), and the appropriate part model is selected, and the appropriate specific dimensions of the platform is further provided to obtain the determined solution that meets the functional requirements.

In order to obtain an appropriate measurement of the rod length and swing angle range to meet the movement of all six first telescopic elements 1444. The end point traversal movement is set as follows: at the beginning of traversal, the telecentric point F with unchanged coordinate in the stationary coordinate system coincides with Fi on the executing rod 1424. Subsequently, the telecentric manipulating assembly 144 advances due to the elongation movement of the first telescopic element 1444, and the telecentric point hereby moves relative to the executing rod 1424, when the end reaches the farthest distance, the telecentric point in the stationary coordinate system coincides with $F_2$ on the executing rod 1424; at each $Z_S$ axial indexing position during the extension of the end of the executing rod 1424, the executing rod 1424 has a gradually increasing deflection angle relative to the stationary coordinate system $Z_S$, and the deflection angle range is 0-20°; corresponding to each $Z_S$ axis direction extension length and each instrument deflection angle, the end has a circular movement on the plane perpendicular to the $Z_S$ axis. Using the idea of differentiation, the executing rod 1424 can theoretically reach any point in the space after the end selects the appropriate subdivision to experience the above traversal movement. At this time, the length and movement swing angle of the first telescopic element 1444 are recorded as the evaluation function for parameter optimization in the traversal movement.

For each first telescopic element 1444, the longest and shortest rod lengths during the traversal movement are recorded to obtain a length change range of each first telescopic element 1444, as illustrated in Formula 30:

$$l_{imin} = \min(L_i), l_{imax} = \max(L_i), l_{i\Delta} = l_{imax} - l_{imin} \quad \text{Formula 30}$$

where $l_i$ is a set of all lengths recorded by a certain first telescopic element 1444, i=1~6.

Similarly, a static hinge swing angle change range is obtained, as illustrated in Formula 31:

$$\alpha_{si\Delta} = A_{simax} - A_{simin} \quad \text{Formula 31}$$

where $a_{simin} = \min(A_{si})$, $a_{simax} = \max(A_{si})$, $A_{si}$ is a set of all static hinge swing angle amplitudes recorded by a certain first telescopic element 1444.

Again, a movable hinge swing angle change range is obtained, as illustrated in Formula 32:

$$\alpha_{mi\Delta} = A_{mimax} - A_{mimin} \quad \text{Formula 32}$$

where $a_{mimin} = \min(A_{mi})$, $a_{mimax} = \max(A_{mi})$, $A_{mi}$ is a set of all movable hinge swing angle amplitudes recorded by a certain rod.

In order to ensure that each first telescopic element 1444 can satisfy the requirements, the maximum value of the length change range of each first telescopic element 1444 is taken:

$$f_{lmax} = \max(l_{1\Delta}, l_{2\Delta}, l_{3\Delta}, l_{4\Delta}, l_{5\Delta}, l_{6\Delta}) \quad \text{Formula 33}$$

$$f_{asmax} = \max(\alpha_{s1\Delta}, \alpha_{s2\Delta}, \alpha_{s3\Delta}, \alpha_{s4\Delta}, \alpha_{s5\Delta}, \alpha_{s6\Delta}) \quad \text{Formula 34}$$

$$f_{ammax} = \max(\alpha_{m1\Delta}, \alpha_{m2\Delta}, \alpha_{m3\Delta}, \alpha_{m4\Delta}, \alpha_{m5\Delta}, \alpha_{m6\Delta}) \quad \text{Formula 35}$$

Parameters related to five sizes of the telecentric manipulating assembly 144 are optimized using a MATLAB genetic algorithm toolbox, and the meanings and ranges of five parameters are shown in Table 4

TABLE 4

Optimization Parameters of Genetic Algorithm

| Optimization Parameters | Minimum Value of Parameter | Maximum Value of Parameter |
|---|---|---|
| Radius of Hinge Point Distribution Circle of Static Platform $r_s$ | 55 mm | 75 mm |
| Radius of Hinge Point Distribution Circle of First Movable Platform $r_m$ | 35 mm | 60 mm |
| Corresponding Center Angle of Adjacent Hinge Points of Static Platform α | 30° | 45° |
| Corresponding Center Angle of Adjacent Hinge Points of Movable Platform β | 30° | 45° |
| Perpendicular Distance Between Movable and Static Platforms (the planes where two groups of hinge points are) h | 150 mm | 300 mm |

In step S1004, fitness functions of the first maximum value, the second maximum value and the third maximum value according to the genetic algorithm; the traversal function is determined according to the size parameter of the telecentric manipulating assembly 144, and the parameter optimization data is obtained according to the traversal function;

different weights are assigned to the maximum value of length change $f_{lmax}$ and the maximum value of swing angle $f_{amax}$ of the first telescopic element 1444 according to the requirements of multi-objective optimization of the genetic algorithm, and are summed to obtain the fitness function $f_{max}$, as shown in Formula 35:

$$f_{max} = w_1 f_{lmax} + w_2 f_{asmax} + w_3 f_{ammax} \quad \text{Formula 35}$$

According to the initial data observation, the length and swing angle range of the first telescopic element 1444 are made in the same order of magnitude, $w_1=1$, $w_2=10$, $w_3=4$.

In step S1006, according to the fitness function and the parameter optimization data, the optimized size of the telecentric manipulating assembly 144 is determined; and the optimized size is used to ensure the requirements for controlling the executing rod 1424 to be met;

corresponding constraints are set during the optimization; in order to ensure the basic performance and movement characteristics of the telecentric manipulating assembly 144, the radius of the hinge distribution circle of the first movable platform 1446 is less than or equal to 0.9 times the radius of the hinge distribution circle of the static platform 1442, and the adjacent included angle of the hinge point of the static platform 1442 is less than the adjacent included angle of the hinge point of the first movable platform 1446, as illustrated in Formula 36:

$$r_m \leq 0.9 r_s, \alpha \leq \beta \quad \text{Formula 36}$$

written in a matrix form of linear constraint, as illustrated in Formula 37;

$$Ax \leq b \quad \text{Formula 37}$$

and $$A = \begin{bmatrix} -0.9 & 1 & 0 & 0 & 0 \\ 0 & 0 & 1 & -1 & 0 \end{bmatrix},$$

$$x = [r_s, r_m, \alpha, \beta, h], b = [0, 0].$$

After the traversal function is written with the five parameters to be optimized as parameter variables, the results obtained by performing optimization five times are shown in Table 5.

TABLE 5

Parameter Optimization Result

Optimization Data

| No. | Convergent Genetic Algebra/Generation | $r_s$/mm | $r_m$/mm | $\alpha/°$ | $\beta/°$ | h/mm | $f_{max}$ |
|---|---|---|---|---|---|---|---|
| 1 | 184 | 55.002 | 35 | 44.996 | 44.998 | 300 | 394.9216 |
| 2 | 211 | 55.002 | 35.001 | 44.997 | 44.999 | 300 | 394.9213 |
| 3 | 231 | 55.003 | 35.002 | 44.981 | 44.996 | 299.998 | 391.9225 |
| Average Value | — | 55.0023 | 35.001 | 44.9986 | 44.9986 | 299.9984 | 391.9218 |

Figure 8:
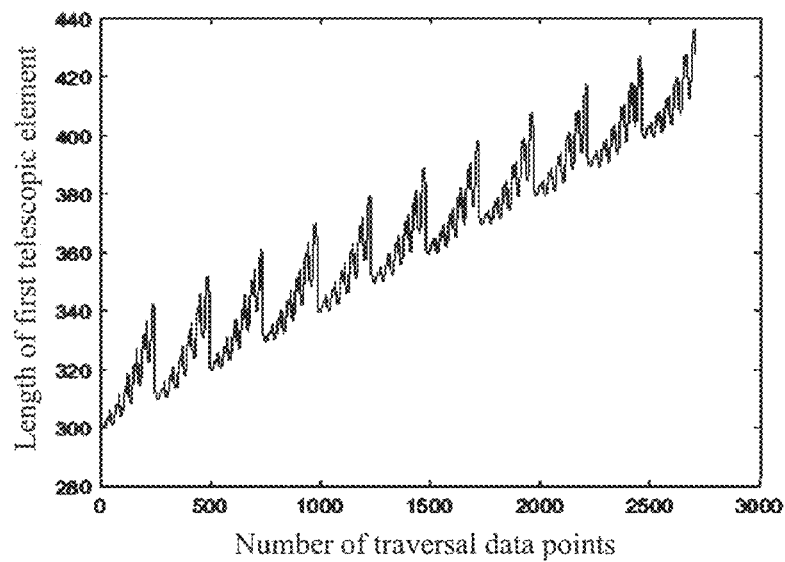
FIG. 8 is a diagram of the length range of a first telescopic element in embodiments of the present disclosure.
Figure 9:
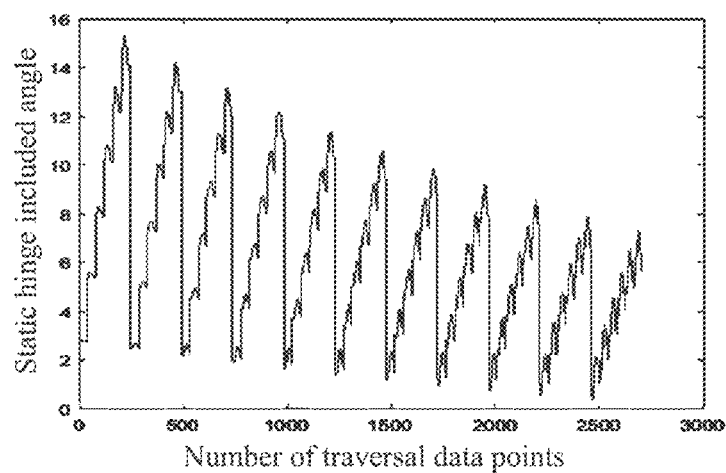
FIG. 9 is a diagram of a static hinge swing angle range in embodiments of the present disclosure.
Figure 10:
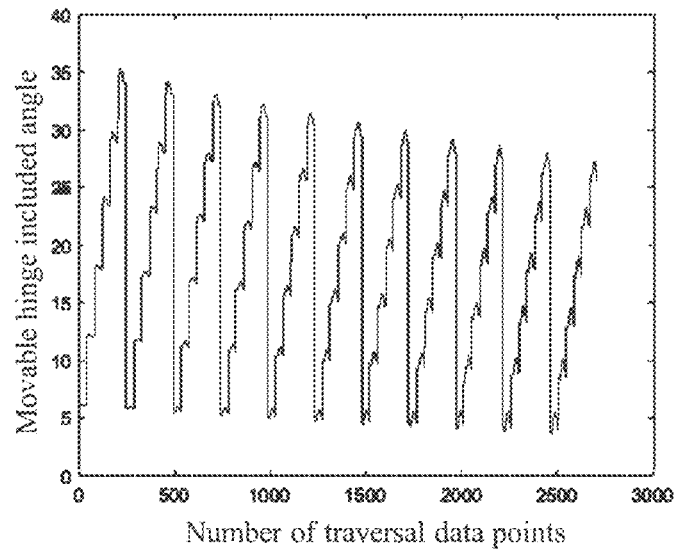
FIG. 10 is a diagram of a movable hinge swing angle range in embodiments of the present disclosure.

According to the data in Table 5, $r_s$=55 mm, $r_m$=35 mm, $\alpha$=45°, $\beta$=45°, h=300 mm, and the length of the first telescopic element 1444 and the swing angle ranges of the movable and static hinges are calculated again under the obtained optimal parameters. FIG. 8 is a diagram of the length of a first telescopic element range in embodiments of the present disclosure, FIG. 9 is a diagram of a static hinge swing angle range in embodiments of the present disclosure, and FIG. 10 is a diagram of a movable hinge swing angle range in embodiments of the present disclosure. The specific data are shown in FIGS. 8 to 10. It can be understood that in the telecentric manipulating assembly 144, the length change trends of the six first telescopic elements 1444 are consistent, the change trends of the six static hinge swing angles are consistent, and the change trends of the six movable hinge swing angles are consistent.

It may be seen according to the data that when the genetic population is in the optimal state, the average values of the five parameters are rounded to 55, 35, 45, 45 and 300, respectively, that is, the upper limit values of the adjacent hinge points of the static platform 1442, the adjacent hinge points of the first movable platform 1446 and the perpendicular distance h of the movable and static platforms 1442 are taken, respectively, and the optimal state can be obtained when the lower limit values of the hinge distribution circle radius $r_s$ of the static platform 1442 and the hinge distribution circle radius $r_m$ of the first movable platform 1446 are taken, respectively. At this time, the length of the first telescopic element 1444 is less than 140 mm, the static hinge swing angle is less than 16°, and the movable hinge swing angle is less than 40°. Considering that the static platform 1442 needs enough space to mount the driving member 1422, the first movable platform 1446 needs to install Hooke hinge pair, and its distribution circle radius cannot be too small, furthermore, in combination with the recommended distribution circle radiuses, $r_s$=70 mm, $r_m$=40 mm, of the first movable platform 1446 and the static platform 1442, and considering that the elongation range of the first telescopic element 1444 is related to the model number of the first telescopic element 1444, it is recommended that the shortest perpendicular distance between the movable platform 144 and the static platform 1442 is 200 mm. Therefore, the optimized recommended parameters, $r_s$=70 mm, $r_m$=40 mm, $\alpha$=45°, $\beta$=45°, h=200 mm, are used in the surgical robotic arm of the embodiments of the present disclosure.

Furthermore, in order to verify the correctness of the method in the embodiments of the present disclosure, Adams simulation verification is carried out. An Adams model is established according to the same size parameters ($r_s$=70 mm, $r_m$=40 mm, $\alpha$=45°, $\beta$=45°, h=200 mm). In the software, the same spiral motion is applied to the end of the executive assembly 142, and the data of the length of each first telescopic element 1444 and the swing angles of the movable and static hinge pairs changing with time are obtained through the inverse solution of the built-in algorithm. It is found through comparison that there is no obvious difference between the two groups of data.

Through the above steps S1002 to S1006, the length range of the first telescopic element 1444, the swing angle range of the movable hinge point and the swing angle range of the static hinge are obtained through the traverse movement of the telecentric fixed point, and the optimization parameters of the telecentric manipulating assembly 144 are obtained according to the maximum length value of the first telescopic element 1444, the maximum swing angle of the movable hinge point and the maximum swing angle of the static hinge point, which ensure that the movement of the first movable platform 1446 will not be restricted during the operation, and improve the operation accuracy.

It should be understood that although respective steps in the flow diagrams of FIG. 2 and FIGS. 4-7 are shown in sequence as indicated by arrows, these steps are not necessarily performed in sequence as indicated by arrows. Unless explicitly stated in the present document, there is no strict sequence restriction for the execution of these steps, and these steps may be carried out in other sequences. Moreover, at least part of the steps in FIG. 2 and FIGS. 4-7 may include a plurality of sub-steps or a plurality of stages, these sub-steps or stages are not necessarily completed in this case, but may be carried out at different times, and the execution sequence of these sub-steps or stages is not necessarily carried out in sequence either, but may be carried out in turn or alternatively with at least part of other steps or sub-steps or stages of other steps.

Figure 11:
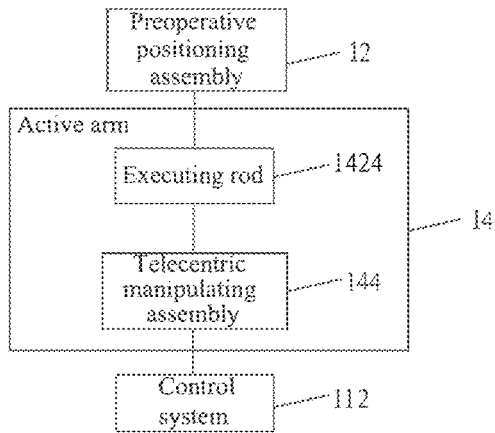
FIG. 11 is a structure block diagram of a surgical robotic arm according to one embodiment of the present disclosure.

In the present embodiment, a surgical robotic arm is provided. FIG. 11 is a structure block diagram of a surgical robotic arm according to one embodiment of the present disclosure, as shown in FIG. 11, the surgical robotic arm includes a preoperative positioning assembly 12, an active arm 14 and a control system 112, the active arm includes an executing rod 1424 and a telecentric manipulating assembly 144, the executing rod 1424 is connected with the telecentric manipulating assembly 144, and the telecentric manipulating assembly 144 is connected with the preoperative positioning assembly 12:

the control system 112 calculates a telecentric fixed point on the executing rod 1424 according to a target point, and controls the preoperative positioning assembly 12 to advance a first movable platform 1446 of the telecentric manipulating assembly 144 along a first coordinate axis of a movable coordinate system, and the advanced distance is equal to a distance from the obtained telecentric manipulating assembly 144 to the minimally invasive opening;

the control system 112 calculates an origin coordinate of an origin of the first movable platform 1446 of the telecentric manipulating assembly 144 in the stationary coordinate system according to the coordinate of the telecentric fixed point and the trajectory coordinate of an end point on the executing rod 1424;

the control system 112 calculates the length of the first telescopic element 1444 of the telecentric manipulating assembly 144 according to the coordinates of a hinge point of the telecentric manipulating assembly 144 in the stationary coordinate system; and the control system 112 controls the first movable platform 1446 to move to a designated pose, and the designated pose is determined according to the origin coordinate and the length of the first telescopic element 1444.

Through the above embodiment, the control system 112 calculates the telecentric fixed point on the executing rod 1424 according to the target point, and performs real time inverse solution according to the telecentric fixed point and the end track of the executing rod 1424 to obtain the pose of the first movable platform 1446, thereby easily realizing online real-time calculation of the inverse solution, and ensuring that the executing rod 1424 has a certain telecentric fixed point when it is deflected at different angles, so as to keep the skin wound not to be cut by the approaching executing rod 1424 during the operation; furthermore, the parallel mechanism formed by the connection of the first movable platform 1446 and the static platform 1442 has a smaller structural size and a greater bearing capacity.

In one embodiment, the control system 112 is further used for, in response to a command of changing the executing rod 1424 is received, controlling the first movable platform 1446 to take the executing rod 1424 to move to be perpendicular to a plane where a minimally invasive opening is, and saving a first coordinate of the end point;

The control system 112 instructs the preoperative positioning assembly 12 to take the first movable platform 1446 to move along the first coordinate axis, and the first movable platform 1446 takes the executing rod 1424 to move to the outside of the minimally invasive opening along the first coordinate axis;

the control system 112, in response to a command of change completion is received, controls the first movable platform 1446 to take the executing rod 1424 to move along the first coordinate axis, and reset the telecentric fixed point to coincide with the minimally invasive opening according to the first coordinate.

Figure 12:
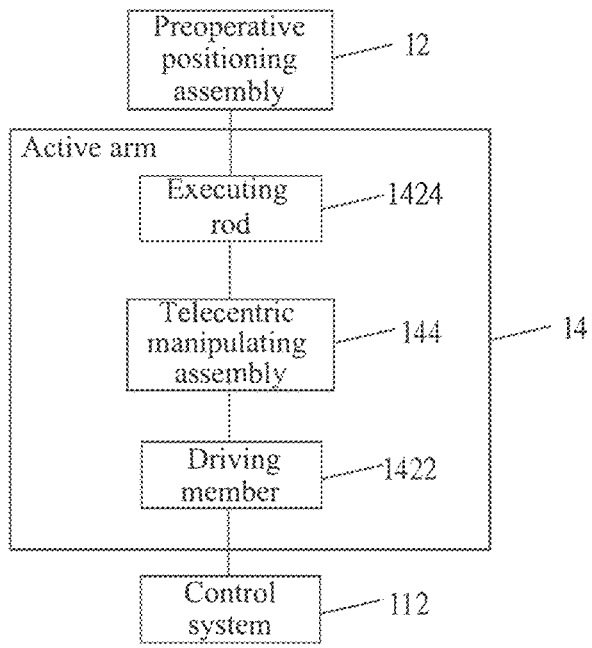
FIG. 12 is a structure block diagram of a surgical robotic arm according to another embodiment of the present disclosure.

In one embodiment, a surgical robotic arm is provided. FIG. 12 is a structure block diagram of a surgical robotic arm according to another embodiment of the present disclosure, as illustrated in FIG. 12, the surgical robotic arm further includes a driving member 1422;

The control system 112 controls the driving member 1422 to drive the surgical instrument 1426 of the executing rod 1424 to move to the designated position along the first coordinate axis, and the driving member 1422 is mounted within the first movable platform 1446.

In one embodiment, a surgical robotic arm is provided, the surgical robotic arm further includes a second movable platform 72 and a second telescopic element 74, and the second movable platform 72 is connected to the first movable platform 72 through the first telescopic element 74 of second level;

the control system 112 calculates a second level origin coordinate of the origin of the second movable platform 72 in the stationary coordinate system and acquire the length of the first telescopic element 74 of second level; the control system 112 determines the pose of the second movable platform 72 according to the second level origin coordinate and the length of the first telescopic element 74 of second level.

In one embodiment, the control system 112, when the telecentric fixed point is traversed from a first end point to a second end point, further calculates a first maximum value, a second maximum value and a third maximum value; and the first maximum value is the maximum value of the length of the first telescopic element 1444, the second maximum value is the maximum swing angle of the static hinge point and the third maximum value is the maximum swing angle of the movable hinge point;

the control system 112 determines the fitness functions of the first maximum value, the second maximum value and the third maximum value according to the genetic algorithm; the control system 112 determines the traversal function according to the size parameter of the telecentric manipulating assembly 144, and the control system 112 obtains the parameter optimization data according to the traversal function;

the control system 112, according to the fitness function and the parameter optimization data, determines the optimized size of the telecentric manipulating assembly 144; and the optimized size is used to ensure the requirements for controlling the executing rod 1424 to be met.

In one embodiment, the ratio of the diameters of the first movable platform 1446 and the static platform 1442 of the telecentric manipulating assembly 144 is between 1:1 and 1:2, which can control the deflection of the first movable platform 1446 to adjust the position of the telecentric fixed point, furthermore, the ratio of the diameters of the first movable platform 1446 and the static platform 1442 adopted in the embodiments of the present disclosure is 1:1.7, thereby improving the stability of the mechanism, and the space volume of the telecentric manipulating assembly 144 is more suitable at this time.

In one embodiment, the six movable hinge points of the first movable platform 1446 of the telecentric manipulating assembly 144 are distributed in pairs, and the included angle between each pair of points ranges from 15° to 60°; the six static hinge points of the static platform 1442 are also distributed in pairs, and the included angle between each pair of points ranges from 60° to 105°. The movable hinge point and the static hinge point are connected sequentially to form the arrangement position of the first telescopic element 1444; and the position arrangement of the first telescopic element 1444 between the first movable platform 1446 and the static platform 1442 forms a parallel mechanism, compared with the Da Vinci robot, which has large stiffness, a stable structure, greater bearing capacity, and is easy to realize online real-time calculation of inverse solution.

Figure 13:
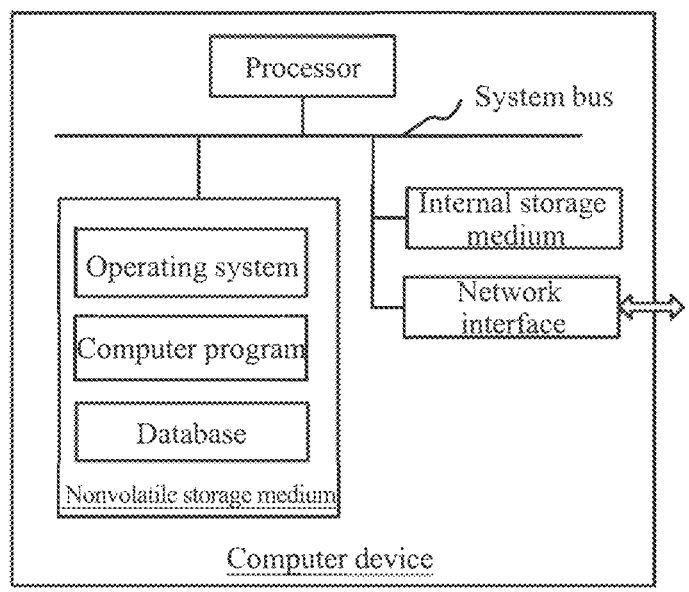
FIG. 13 is an internal structural diagram of a computer device according to embodiments of the present disclosure.

In one embodiment, a computer device is provided, and the computer device may be a server. FIG. 13 is an internal structural diagram of a computer device according to embodiments of the present disclosure, as illustrated in FIG. 13. The computer device includes a processor, a memory, a network interface and a database connected through a system bus, and the processor of the computer device is used to provide calculation and control capabilities. The memory of the computer device includes a nonvolatile storage medium and an internal memory. The nonvolatile storage medium stores an operating system, a computer program, and a database. The internal memory provides an environment for the operation of the operating system and computer program in the nonvolatile storage medium. The database of the computer device is used for storing the telecentric fixed point related data. The network interface of the computer device is used for communicating with external terminals through network connection. The computer program is executed by the processor to realize a control method for a surgical robotic arm.

It can be understood by those skilled in the art that the structure shown in FIG. 13 is only a block diagram of some structures related to the solution of the present disclosure, and does not constitute a limitation to the computer device to which the solution of the present disclosure is applied, and the specific computer device may include more or less components than those shown in the figure, or combine some components, or have different component arrangements.

In one embodiment, a computer device is provided and includes a memory, a processor and a computer program which is stored on the memory and may run on the processor, and the processor implements the steps in the control method for a surgical robotic arm provided by the above respective embodiments while executing the computer program.

In one embodiment, a computer readable storage medium is provided, on which a computer program is stored, and the computer program implements the steps in the control method for a surgical robotic arm provided by the above respective embodiments while being executed by the processor.

A control method for a surgical robotic arm, a computer device and a surgical robotic arm are provided according to various embodiments of the present disclosure.

According to various embodiments of the present disclosure, a control method for a surgical robotic arm is provided, the surgical robotic arm includes a preoperative positioning assembly and an active arm, the active arm includes an executing rod and a telecentric manipulating assembly, the executing rod is connected to the telecentric manipulating assembly and the telecentric manipulating assembly is connected to the preoperative positioning assembly. The method includes:
  calculating a telecentric fixed point on the executing rod according to a target point, and controlling the preoperative positioning assembly to advance a first movable platform of the telecentric manipulating assembly along a first coordinate axis of a movable coordinate system, and the advanced distance is equal to a distance from the obtained telecentric fixed point to an end point on the executing assembly;
  calculating a first origin coordinate of an origin of the first movable platform in a stationary coordinate system according to the coordinate of the telecentric fixed point and the trajectory coordinate of the end point;
  calculating the length of a first telescopic element of the telecentric manipulating assembly according to the coordinates of a hinge point of the telecentric manipulating assembly in the stationary coordinate system; and
  controlling the first movable platform to move to a designated pose, and the designated pose is determined according to the first origin coordinate and the length of the first telescopic element.

In one embodiment therein, the method after the controlling the first movable platform to move to a designated pose includes:
  moving the telecentric fixed point, and re-determining the designated pose according to the coordinate of the moved telecentric fixed point, and the telecentric fixed point moves within a preset range.

In one embodiment therein, the moving the telecentric fixed point includes at least one of:
  in case of controlling the first movable platform to take the executing rod to move to be perpendicular to a plane where a minimally invasive opening is, controlling the preoperative positioning assembly to take the telecentric manipulating assembly to move along the first coordinate axis; or
  controlling the first movable platform to move, the movement being used for moving the telecentric fixed point.

In one embodiment therein, the calculating a first origin coordinate of an origin of the first movable platform in a stationary coordinate system according to the coordinate of the telecentric fixed point and the trajectory coordinate of the end point includes:
  determining a first calculation model according to the relationship among the coordinate of the telecentric fixed point, the trajectory coordinate and a direction vector module length, the direction vector module length being a direction vector module length of the executing rod in the stationary coordinate system;
  determining a second calculation model according to a positional relationship among the coordinate of the telecentric fixed point, the trajectory coordinate and the first origin coordinate;
  determining a third calculation model according to a distance formula between the trajectory coordinate and the first origin coordinate; and
  determining the first origin coordinate according to the first calculation model, the second calculation model and the third calculation model.

In one embodiment therein, the calculating the length of the first telescopic element of the telecentric manipulating assembly according to the coordinates of a hinge point of the telecentric manipulating assembly in the stationary coordinate system includes:
  determining a first transformation matrix according to a first rotational angle and a second rotational angle, and the first rotational angle is an angle that the executing rod rotates about a second coordinate axis, and the second rotational angle is an angle that the executing rod rotates about a third coordinate axis;
  determining a first coordinate according to the first transformation matrix, and calculating the length of the first telescopic element of the telecentric manipulating assembly according to the first coordinate and the second coordinate, and the first coordinate is a coordinate of a movable hinge point in the stationary coordinate system, the second coordinate is a coordinate of a static hinge point in the stationary coordinate system, the movable hinge point is positioned on the first movable platform, and the static hinge point is positioned on a static platform of the telecentric manipulating assembly.

In one embodiment, the determining a first coordinate according to the first transformation matrix, and the calculating the length of the first telescopic element of the telecentric manipulating assembly according to the first coordinate and the second coordinate includes:
  acquiring a first homogeneous coordinate of the movable hinge point in the movable coordinate system according to the first origin coordinate and a third rotational angle; acquiring a second homogeneous coordinate of the static hinge point in the stationary coordinate system according to the first origin coordinate and a fourth rotational angle, and the third rotational angle is an angle that the movable hinge point rotates about the first movable platform origin, and the fourth rotational angle is an angle that the static hinge point rotates about the static platform origin;

determining a second transformation matrix according to the first transformation matrix and the first origin coordinate, and acquiring a third homogeneous coordinate of the movable hinge point in the stationary coordinate system according to the second transformation matrix and the first homogeneous coordinate; and calculating the length of the first telescopic element of the telecentric manipulating assembly according to the second homogeneous coordinate and the third homogeneous coordinate.

In one embodiment therein, the method after the controlling the first movable platform to move to a designated pose includes:

in the case where the telecentric manipulating assembly further includes a second movable platform and a plurality of second telescopic elements disposed between the first movable platform and the second movable platform, and the second movable platform is connected to the executing assembly, calculating a second origin coordinate of the origin of the second movable platform in the stationary coordinate system and acquire the length of a second telescopic element; and determining a pose of the second movable platform according to the second origin coordinate and the length of the second telescopic element.

In one embodiment therein, the method before the calculating a second origin coordinate of an origin of the second movable platform in the stationary coordinate system and acquiring the length of the second telescopic element includes:

in the case where a calculated deflection angle of the first movable platform is within a second level opening boundary, setting the second movable platform to a locked state; and in the case where the calculated deflection angle is larger than the second level opening boundary, unlocking the second movable platform to move.

In one embodiment therein, the unlocking the second movable platform to move includes:

a first plane and a second plane being within the same one plane, and the first plane is a plane formed by the normal of the deflection angle of the second movable platform and the telecentric fixed point, and the second plane is a plane formed by the normal of the deflection angle of the first movable platform and the telecentric fixed point.

In one embodiment therein, the method after the controlling the first movable platform to move to a designated pose includes:

controlling a rotational driving member to drive the executing assembly to rotate along an axial direction of the executing rod, the rotational driving member is mounted within the first movable platform.

In one embodiment therein, the method after the controlling the first movable platform to move to a designated pose includes:

controlling a first deflection driving member and a second deflection driving member to drive a built-in transmission cable of the executing assembly, to respectively bring surgical instruments of the executing assembly to deflect toward two staggered different directions; and controlling an opening and closing driving member to the transmission cable to bring the opening and closing of the surgical instruments; and the first deflection driving member, the second deflection driving member and the opening and closing driving member are mounted within the executing rod.

In one embodiment therein, the method after the controlling the first movable platform to move to a designated pose includes:

in response to a command of changing the executing rod is received, controlling the first movable platform to take the executing rod to move to be perpendicular to a plane where a minimally invasive opening is, and saving a third coordinate of the end point;

indicating the preoperative positioning assembly to take the first movable platform to move along the first coordinate axis, the first movable platform taking the executing rod to move along the first coordinate axis to an outer side of the minimally invasive opening; and in response to a command of change completion is received, controlling the telecentric manipulating assembly to reset according to the third coordinate.

According to various embodiments of the present disclosure, a surgical robotic arm is provided and includes a preoperative positioning assembly, a telecentric manipulating assembly, an executing assembly and a control system. The preoperative positioning assembly is connected to the telecentric manipulating assembly. The telecentric manipulating assembly is connected to the executing assembly;

the control system calculates a telecentric fixed point on the executing rod of the executing assembly according to a target point, and controls the preoperative positioning assembly to advance a first movable platform of the telecentric manipulating assembly along a first coordinate axis of a movable coordinate system, and the advanced distance is equal to a distance from the obtained telecentric fixed point to an end point on the executing assembly;

the control system calculates a first origin coordinate of an origin of the first movable platform in a stationary coordinate system according to the coordinate of the telecentric fixed point and the trajectory coordinate of the end point;

the control system calculates the length of the first telescopic element of the telecentric manipulating assembly according to the coordinates of a hinge point of the telecentric manipulating assembly in the stationary coordinate system; and the control system controls the first movable platform to move to a designated pose, and the designated pose is determined according to the first origin coordinate and the length of the first telescopic element.

In one embodiment therein, the surgical robotic arm further includes a rotational driving member;

the control system controls the rotational driving member to drive the executing assembly to rotate along an axial direction of the executing rod, and the rotational driving member is mounted within the first movable platform.

In one embodiment therein, the telecentric manipulating assembly includes multi-level interconnected parallel platforms, each level of which includes two opposite platforms and telescopic elements between the two platforms;

and the parallel platforms in the multi-level parallel platforms relatively close to the preoperative positioning assembly are first level parallel platforms, and the first level parallel platforms include a static platform, the first movable platform and a plurality of first telescopic elements disposed between the static platform and the first movable platform.

In one embodiment therein, the number of levels of the parallel platforms is two, the telecentric manipulating assembly further includes second level parallel platforms connected to the first level parallel platforms, and the second level parallel platforms include a second movable platform and a plurality of second telescopic elements disposed between the first movable platform and the second movable platform; one side of the second movable platform relatively far away from the static platform of the telecentric manipulating assembly is fixedly connected to the executing assembly; both ends of each of the second telescopic element are rotationally connected to the first movable platform and the second movable platform, respectively;

the control system calculates a second origin coordinate of the origin of the second movable platform in the stationary coordinate system and acquire the length of the second telescopic element; and determines a pose of the second movable platform according to the second origin coordinate and the length of the second telescopic element.

According to various embodiments of the present disclosure, a computer device is provided and includes a memory, a processor and a computer program which is stored on the memory and may run on the processor, and the processor implements steps of any method according to various embodiments of the present disclosure while executing the computer program.

According to various embodiments of the present disclosure, a computer readable storage medium is provided, on which a computer program is stored, and the computer program implements steps of any method according to various embodiments of the present disclosure while being executed by a processor.

Through various embodiments of the present disclosure, a control method for a surgical robotic arm is adopted, in which a telecentric fixed point on the executing rod is calculated according to a target point, and the preoperative positioning assembly is controlled to advance a first movable platform of the telecentric manipulating assembly along a first coordinate axis of a movable coordinate system; a first origin coordinate of an origin of the first movable platform in a stationary coordinate system is calculated according to the coordinate of the telecentric fixed point and the trajectory coordinate of the end point; the length of the first telescopic element of the telecentric manipulating assembly is calculated according to the coordinates of a hinge point of the telecentric manipulating assembly in the stationary coordinate system; and the first movable platform is controlled to move to the designated pose, and the designated pose is determined according to the first origin coordinate and the length of the first telescopic element, thereby realizing the telecentric fixed point, and solving the problems of the large structural dimensions of the surgical robotic arm and the interference between the surgical robotic arms.

Those ordinary skilled in the art may understand the all or part of the processes in the method of the above embodiments can be completed by instructing relevant hardware through a computer program, the computer program may be stored in a nonvolatile computer readable storage medium, when the computer program is executed, it may include the processes of the embodiments of the above method. Any reference to a memory, storage, database or other media used in respective embodiments provided by the present disclosure may include at least one of nonvolatile memory or volatile memory. The nonvolatile memory may include a read only memory (ROM), a programmable ROM (PROM), an electrically programmable ROM (EPROM), an electrically erasable programmable ROM (EEPROM), or a flash memory. The volatile memory may include a random access memory (RAM) or an external cache memory. As an illustration rather than a limitation, RAM is available in various forms, such as a static RAM (SRAM), a dynamic RAM (DRAM), a synchronous DRAM (SDRAM), a dual data rate SDRAM (DDRSDRAM), an enhanced SDRAM (ESDRAM), a synchronous link (Synchlink) DRAM (SLDRAM), a Rambus direct RAM (RDRAM), a direct memory bus dynamic RAM (DRDRAM), a memory bus dynamic RAM (RDRAM), etc.

Respective technical features of the above embodiments may be combined arbitrarily. In order to simplify the description, all possible combinations of respective technical features in the above embodiments are not described. However, as long as there is no contradiction in the combination of these technical features, it should be considered as the scope of the description.

The above embodiments only express several embodiments of the present disclosure, and the descriptions are more specific and detailed, but it cannot be understood as a limitation on the scope of the patent application. It should be noted that for those ordinary skilled in the art, several modifications and improvements may be further made without departing from the concept of the present disclosure, which all belong to the protection scope of the present disclosure. Therefore, the scope of protection of the present disclosure for patent shall be subject to the appended claims.

What is claimed is:

1. A control method for a surgical robotic arm which comprises a preoperative positioning assembly, a telecentric manipulating assembly which comprises a parallel mechanism comprising a first movable platform, a static platform and a first telescopic element, and an executing assembly comprising an executing rod, the preoperative positioning assembly being connected to the telecentric manipulating assembly, and the telecentric manipulating assembly being connected to the executing assembly, comprising:

calculating a telecentric fixed point on the executing rod according to a target point;

controlling the preoperative positioning assembly to advance the first movable platform along a first coordinate axis of a movable coordinate system, wherein the advanced distance is equal to a distance from an end point on the executing assembly to the telecentric fixed point;

calculating a first origin coordinate of an origin of the first movable platform in a stationary coordinate system according to the coordinate of the telecentric fixed point and a trajectory coordinate of the end point;

calculating a length of the first telescopic element according to the coordinates of a movable hinge point and a static hinge point of the telecentric manipulating assembly in the stationary coordinate system, wherein the movable hinge point is positioned on the first movable platform, and the static hinge point is positioned on the static platform; and controlling the first movable platform to move to a designated pose, wherein the designated pose is determined according to the first origin coordinate and the length of the first telescopic element.

2. The method of claim 1, wherein the method further comprises: moving the telecentric fixed point, and re-determining the designated pose according to the coordinate of the moved telecentric fixed point, wherein the telecentric fixed point moves within a preset range.

3. The method of claim 2, wherein the moving the telecentric fixed point comprises at least one of
in case of controlling the first movable platform to take the executing rod to move to be perpendicular to a plane where a minimally invasive opening is, controlling the preoperative positioning assembly to take the telecentric manipulating assembly to move along the first coordinate axis; or
controlling the first movable platform to move, the movement being used for moving the telecentric fixed point.

4. The method of claim 1, wherein the calculating a first origin coordinate of an origin of the first movable platform in a stationary coordinate system according to the coordinate of the telecentric fixed point and the trajectory coordinate of the end point comprises:
determining a first calculation model according to the relationship among the coordinate of the telecentric fixed point, the trajectory coordinate and a direction vector module length, the direction vector module length being a direction vector module length of the executing rod in the stationary coordinate system;
determining a second calculation model according to a positional relationship among the coordinate of the telecentric fixed point, the trajectory coordinate and the first origin coordinate;
determining a third calculation model according to a distance formula between the trajectory coordinate and the first origin coordinate; and
determining the first origin coordinate according to the first calculation model, the second calculation model and the third calculation model.

5. The method of claim 1, wherein the calculating the length of the first telescopic element according to the coordinates of the movable hinge point and the static hinge point of the telecentric manipulating assembly in the stationary coordinate system comprises:
determining a first transformation matrix according to a first rotational angle and a second rotational angle, wherein the first rotational angle is an angle that the executing rod rotates about a second coordinate axis, and the second rotational angle is an angle that the executing rod rotates about a third coordinate axis;
determining a first coordinate according to the first transformation matrix, and calculating the length of the first telescopic element according to the first coordinate and the second coordinate,
wherein the first coordinate is a coordinate of the movable hinge point in the stationary coordinate system, the second coordinate is a coordinate of the static hinge point in the stationary coordinate system.

6. The method of claim 5, wherein the determining a first coordinate according to the first transformation matrix, and calculating the length of the first telescopic element according to the first coordinate and the second coordinate comprises:
acquiring a first homogeneous coordinate of the movable hinge point in the movable coordinate system according to the first origin coordinate and a third rotational angle; acquiring a second homogeneous coordinate of the static hinge point in the stationary coordinate system according to the first origin coordinate and a fourth rotational angle,
wherein the third rotational angle is an angle that the movable hinge point rotates about the first movable platform origin, and the fourth rotational angle is an angle that the static hinge point rotates about the static platform origin;
determining a second transformation matrix according to the first transformation matrix and the first origin coordinate, and acquiring a third homogeneous coordinate of the movable hinge point in the stationary coordinate system according to the second transformation matrix and the first homogeneous coordinate; and
calculating the length of the first telescopic element according to the second homogeneous coordinate and the third homogeneous coordinate.

7. The method of claim 1, wherein the method after the controlling the first movable platform to move to a designated pose comprises:
in the case where the telecentric manipulating assembly further comprises a second movable platform and a plurality of second telescopic elements disposed between the first movable platform and the second movable platform, and the second movable platform is connected to the executing assembly, calculating a second origin coordinate of an origin of the second movable platform in the stationary coordinate system and acquiring a length of the second telescopic element; and
determining a pose of the second movable platform according to the second origin coordinate and the length of the second telescopic element.

8. The method of claim 7, wherein the method before the calculating a second origin coordinate of an origin of the second movable platform in the stationary coordinate system and acquiring the length of the second telescopic element comprises:
in the case where a calculated deflection angle of the first movable platform is within a second level opening boundary, setting the second movable platform to a locked state; and
in the case where the calculated deflection angle is larger than the second level opening boundary, unlocking the second movable platform to move.

9. The method of claim 8, wherein the unlocking the second movable platform to move comprises:
a first plane and a second plane being within the same one plane, wherein the first plane is a plane formed by the normal of the deflection angle of the second movable platform and the telecentric fixed point, and the second plane is a plane formed by the normal of the deflection angle of the first movable platform and the telecentric fixed point.

10. The method of claim 1, wherein the method after the controlling the first movable platform to move to a designated pose comprises:
controlling a rotational driving member to drive the executing assembly to rotate along an axial direction of the executing rod, the rotational driving member is mounted within the first movable platform.

11. The method of claim 10, wherein the executing assembly further comprises a driving member and a surgical instrument, and the driving member comprises a first deflection driving member, a second deflection driving member and an opening and closing driving member,
wherein the method after the controlling the first movable platform to move to a designated pose comprises:
controlling the first deflection driving member and the second deflection driving member to drive a built-in transmission cable of the executing assembly, to respectively bring the surgical instrument to deflect toward two staggered different directions; and controlling the opening and closing driving member to drive the transmission cable to bring the opening and closing of the surgical instrument; wherein the first deflection driving member, the second deflection driving member and the opening and closing driving member are mounted at the connection between the executing assembly and the first movable platform, the first deflection driving member and the second deflection driving member each comprise a motor.

12. The method of claim 1, wherein the method after the controlling the first movable platform to move to a designated pose comprises:

in response to a command of changing the executing rod is received, controlling the first movable platform to take the executing rod to move to be perpendicular to a plane where a minimally invasive opening is, and saving a third coordinate of the end point;

indicating the preoperative positioning assembly to take the first movable platform to move along the first coordinate axis, the first movable platform taking the executing rod to move along the first coordinate axis to an outer side of the minimally invasive opening; and in response to a command of change completion is received, controlling the telecentric manipulating assembly to reset according to the third coordinate.

13. The method of claim 1, wherein the method before calculating a telecentric fixed point on the executing rod of the surgical robot according to a target point comprises:

when the telecentric fixed point is traversed from a first end point to a second end point, calculating a first maximum value, a second maximum value and a third maximum value, wherein the first maximum value is the maximum value of the length of the first telescopic element, the second maximum value is the maximum swing angle of the static hinge point and the third maximum value is the maximum swing angle of the movable hinge point;

determining fitness functions of the first maximum value, the second maximum value and the third maximum value according to a genetic algorithm; determining a traversal function according to the size parameter of the telecentric manipulating assembly, and obtaining parameter optimization data according to the traversal function; and determining the optimized size of the telecentric manipulating assembly according to the fitness function and the parameter optimization data, wherein the optimized size is used to ensure the requirements for controlling the executing rod to be met.

14. A surgical robotic arm which comprises a preoperative positioning assembly, a telecentric manipulating assembly which comprises a parallel mechanism comprising a first movable platform, a static platform and a first telescopic element, an executing assembly comprising an executing rod, and a control system, the preoperative positioning assembly being connected to the telecentric manipulating assembly, and the telecentric manipulating assembly being connected to the executing assembly;

the control system calculates a telecentric fixed point on the executing rod according to a target point, and controls the preoperative positioning assembly to advance the first movable platform along a first coordinate axis of a movable coordinate system, wherein the advanced distance is equal to a distance from the obtained telecentric fixed point to an end point on the executing assembly;

the control system calculates a first origin coordinate of an origin of the first movable platform in a stationary coordinate system according to the coordinate of the telecentric fixed point and a trajectory coordinate of the end point;

the control system calculates a length of the first telescopic element according to the coordinates of a movable hinge point and a static hinge point of the telecentric manipulating assembly in the stationary coordinate system, wherein the movable hinge point is positioned on the first movable platform, and the static hinge point is positioned on the static platform; and the control system controls the first movable platform to move to a designated pose, wherein the designated pose is determined according to the first origin coordinate and the length of the first telescopic element.

15. The surgical robotic arm of claim 14, wherein the surgical robotic arm further comprises a rotational driving member; the control system controls the rotational driving member to drive the executing assembly to rotate along an axial direction of the executing rod, and the rotational driving member is mounted within the first movable platform.

16. The surgical robotic arm of claim 14, wherein the telecentric manipulating assembly comprises multi-level interconnected parallel platforms, each level of which comprises two opposite platforms and telescopic elements between the two platforms;

wherein the parallel platforms in the multi-level parallel platforms relatively close to the preoperative positioning assembly are first level parallel platforms, and the first level parallel platforms comprise the static platform, the first movable platform and a plurality of first telescopic elements disposed between the static platform and the first movable platform.

17. The surgical robotic arm of claim 16, wherein the number of levels of the parallel platforms is two, the telecentric manipulating assembly further comprises second level parallel platforms connected to the first level parallel platforms, and the second level parallel platforms comprise a second movable platform and a plurality of second telescopic elements disposed between the first movable platform and the second movable platform; one side of the second movable platform relatively far away from the static platform of the telecentric manipulating assembly is fixedly connected to the executing assembly; both ends of each of the second telescopic element are rotationally connected to the first movable platform and the second movable platform, respectively;

the control system calculates a second origin coordinate of an origin of the second movable platform in the stationary coordinate system and acquire a length of the second telescopic element; and determines a pose of the second movable platform according to the second origin coordinate and the length of the second telescopic element.

18. A computer device, comprising a memory, a processor and a computer program which is stored on the memory and is capable of running on a processor, wherein the processor implements steps of a control method for a surgical robot arm while executing the computer program, wherein the surgical robotic arm comprises a preoperative positioning assembly, a telecentric manipulating assembly which comprises a parallel mechanism comprising a first movable platform, a static platform and a first telescopic element, and an executing assembly comprising an executing rod, the preoperative positioning assembly is connected to the telecentric manipulating assembly, and the telecentric manipulating assembly is connected to the executing assembly, wherein the control method comprises:

calculating a telecentric fixed point on the executing rod according to a target point;

controlling the preoperative positioning assembly to advance the first movable platform along a first coordinate axis of a movable coordinate system, wherein the advanced distance is equal to a distance from an end point on the executing assembly to the telecentric fixed point;

calculating a first origin coordinate of an origin of the first movable platform in a stationary coordinate system according to the coordinate of the telecentric fixed point and a trajectory coordinate of the end point;

calculating a length of the first telescopic element according to the coordinates of a movable hinge point and a static hinge point of the telecentric manipulating assembly in the stationary coordinate system, wherein the movable hinge point is positioned on the first movable platform, and the static hinge point is positioned on the static platform; and controlling the first movable platform to move to a designated pose, wherein the designated pose is determined according to the first origin coordinate and the length of the first telescopic element.

19. A non-transitory computer readable storage medium storing a computer program thereon, wherein the computer program implements steps of a control method for a surgical robot arm while being executed by a processor, wherein the surgical robotic arm comprises a preoperative positioning assembly, a telecentric manipulating assembly which comprises a parallel mechanism comprising a first movable platform, a static platform and a first telescopic element, and an executing assembly comprising an executing rod, the preoperative positioning assembly is connected to the telecentric manipulating assembly, and the telecentric manipulating assembly is connected to the executing assembly, wherein the control method comprises:

calculating a telecentric fixed point on the executing rod according to a target point;

controlling the preoperative positioning assembly to advance the first movable platform along a first coordinate axis of a movable coordinate system, wherein the advanced distance is equal to a distance from an end point on the executing assembly to the telecentric fixed point;

calculating a first origin coordinate of an origin of the first movable platform in a stationary coordinate system according to the coordinate of the telecentric fixed point and a trajectory coordinate of the end point;

calculating a length of the first telescopic element according to the coordinates of a movable hinge point and a static hinge point of the telecentric manipulating assembly in the stationary coordinate system, wherein the movable hinge point is positioned on the first movable platform, and the static hinge point is positioned on the static platform; and controlling the first movable platform to move to a designated pose, wherein the designated pose is determined according to the first origin coordinate and the length of the first telescopic element.

20. The computer device of claim 18, wherein the method further comprises:

moving the telecentric fixed point, and re-determining the designated pose according to the coordinate of the moved telecentric fixed point, wherein the telecentric fixed point moves within a preset range.

21. The computer device of claim 18, wherein the calculating the length of the first telescopic element according to the coordinates of the movable hinge point and the static hinge point of the telecentric manipulating assembly in the stationary coordinate system comprises:

determining a first transformation matrix according to a first rotational angle and a second rotational angle, wherein the first rotational angle is an angle that the executing rod rotates about a second coordinate axis, and the second rotational angle is an angle that the executing rod rotates about a third coordinate axis;

determining a first coordinate according to the first transformation matrix, and calculating the length of the first telescopic element according to the first coordinate and the second coordinate, wherein the first coordinate is a coordinate of the movable hinge point in the stationary coordinate system, the second coordinate is a coordinate of the static hinge point in the stationary coordinate system.

22. The computer device of claim 18, wherein the method after the controlling the first movable platform to move to a designated pose comprises:

in the case where the telecentric manipulating assembly further comprises a second movable platform and a plurality of second telescopic elements disposed between the first movable platform and the second movable platform, and the second movable platform is connected to the executing assembly, calculating a second origin coordinate of an origin of the second movable platform in the stationary coordinate system and acquiring a length of the second telescopic element; and determining a pose of the second movable platform according to the second origin coordinate and the length of the second telescopic element.

23. The computer device of claim 18, wherein the method after the controlling the first movable platform to move to a designated pose comprises:

in response to a command of changing the executing rod is received, controlling the first movable platform to take the executing rod to move to be perpendicular to a plane where a minimally invasive opening is, and saving a third coordinate of the end point;

indicating the preoperative positioning assembly to take the first movable platform to move along the first coordinate axis, the first movable platform taking the executing rod to move along the first coordinate axis to an outer side of the minimally invasive opening; and in response to a command of change completion is received, controlling the telecentric manipulating assembly to reset according to the third coordinate.

24. The computer device of claim 18, wherein the method before calculating a telecentric fixed point on the executing rod of the surgical robot according to a target point comprises:

when the telecentric fixed point is traversed from a first end point to a second end point, calculating a first maximum value, a second maximum value and a third maximum value, wherein the first maximum value is the maximum value of the length of the first telescopic element, the second maximum value is the maximum swing angle of the static hinge point and the third maximum value is the maximum swing angle of the movable hinge point;

determining fitness functions of the first maximum value, the second maximum value and the third maximum value according to a genetic algorithm; determining a traversal function according to the size parameter of the telecentric manipulating assembly, and obtaining parameter optimization data according to the traversal function; and determining the optimized size of the telecentric manipulating assembly according to the fitness function and the parameter optimization data, wherein the optimized size is used to ensure the requirements for controlling the executing rod to be met.

25. The non-transitory computer readable storage medium of claim 19, wherein the method further comprises: moving the telecentric fixed point, and re-determining the designated pose according to the coordinate of the moved telecentric fixed point, wherein the telecentric fixed point moves within a preset range.

26. The non-transitory computer readable storage medium of claim 19, wherein the calculating the length of the first telescopic element according to the coordinates of the movable hinge point and the static hinge point of the telecentric manipulating assembly in the stationary coordinate system comprises:

determining a first transformation matrix according to a first rotational angle and a second rotational angle, wherein the first rotational angle is an angle that the executing rod rotates about a second coordinate axis, and the second rotational angle is an angle that the executing rod rotates about a third coordinate axis;

determining a first coordinate according to the first transformation matrix, and calculating the length of the first telescopic element according to the first coordinate and the second coordinate, wherein the first coordinate is a coordinate of the movable hinge point in the stationary coordinate system, the second coordinate is a coordinate of the static hinge point in the stationary coordinate system.

27. The non-transitory computer readable storage medium of claim 19, wherein the method after the controlling the first movable platform to move to a designated pose comprises:

in the case where the telecentric manipulating assembly further comprises a second movable platform and a plurality of second telescopic elements disposed between the first movable platform and the second movable platform, and the second movable platform is connected to the executing assembly, calculating a second origin coordinate of an origin of the second movable platform in the stationary coordinate system and acquiring a length of the second telescopic element; and determining a pose of the second movable platform according to the second origin coordinate and the length of the second telescopic element.

28. The non-transitory computer readable storage medium of claim 19, wherein the method after the controlling the first movable platform to move to a designated pose comprises:

in response to a command of changing the executing rod is received, controlling the first movable platform to take the executing rod to move to be perpendicular to a plane where a minimally invasive opening is, and saving a third coordinate of the end point;

indicating the preoperative positioning assembly to take the first movable platform to move along the first coordinate axis, the first movable platform taking the executing rod to move along the first coordinate axis to an outer side of the minimally invasive opening; and in response to a command of change completion is received, controlling the telecentric manipulating assembly to reset according to the third coordinate.

29. The non-transitory computer readable storage medium of claim 19, wherein the method before calculating a telecentric fixed point on the executing rod of the surgical robot according to a target point comprises:

when the telecentric fixed point is traversed from a first end point to a second end point, calculating a first maximum value, a second maximum value and a third maximum value, wherein the first maximum value is the maximum value of the length of the first telescopic element, the second maximum value is the maximum swing angle of the static hinge point and the third maximum value is the maximum swing angle of the movable hinge point;

determining fitness functions of the first maximum value, the second maximum value and the third maximum value according to a genetic algorithm; determining a traversal function according to the size parameter of the telecentric manipulating assembly, and obtaining parameter optimization data according to the traversal function; and determining the optimized size of the telecentric manipulating assembly according to the fitness function and the parameter optimization data, wherein the optimized size is used to ensure the requirements for controlling the executing rod to be met.

* * * * *